US009907681B2

(12) United States Patent
Tobis et al.

(10) Patent No.: US 9,907,681 B2
(45) Date of Patent: Mar. 6, 2018

(54) STENT WITH TETHER INTERFACE

(71) Applicant: 4 TECH INC., Waltham, MA (US)

(72) Inventors: Idan Tobis, Beth Hashmonai (IL); Charlotte Murphy, Ardrahan (IE); Michael Gilmore, Ardrahan (IE)

(73) Assignee: 4TECH INC., Waltham, MA (US)

( * ) Notice: Subject to any disclaimer, the term of this patent is extended or adjusted under 35 U.S.C. 154(b) by 0 days.

(21) Appl. No.: 14/773,640

(22) PCT Filed: Mar. 9, 2014

(86) PCT No.: PCT/IL2014/050233
§ 371 (c)(1),
(2) Date: Sep. 8, 2015

(87) PCT Pub. No.: WO2014/141239
PCT Pub. Date: Sep. 18, 2014

(65) Prior Publication Data
US 2016/0022448 A1    Jan. 28, 2016

Related U.S. Application Data

(60) Provisional application No. 61/783,224, filed on Mar. 14, 2013.

(51) Int. Cl.
*A61F 2/915* (2013.01)
*A61F 2/88* (2006.01)
(Continued)

(52) U.S. Cl.
CPC ............ *A61F 2/88* (2013.01); *A61B 17/0401* (2013.01); *A61F 2/848* (2013.01);
(Continued)

(58) Field of Classification Search
CPC .......... A61F 2/88; A61F 2/848; A61F 2/2418; A61F 2/2451; A61F 2/2487;
(Continued)

(56) References Cited

U.S. PATENT DOCUMENTS 4,214,349 A    7/1980 Munch
4,405,313 A    9/1983 Sisley et al.
(Continued)

FOREIGN PATENT DOCUMENTS

DE    102007043830    4/2009
EP    1568326    8/2005
(Continued)

OTHER PUBLICATIONS

A non-final office action in U.S. Appl. No. 13/574,088, dated Mar. 23, 2017.
(Continued)

*Primary Examiner* — Brian Pellegrino
*Assistant Examiner* — Seema Mathew
(74) *Attorney, Agent, or Firm* — UltimatEdge IP Law Group, P.C.; Dean G. Stathakis; Vito A. Canuso, III

(57) ABSTRACT

A radially-expandable stent (20) is shaped so as to define one or more tether interfaces (50), a lower-securement portion (56), and a higher-securement portion (64). The lower-securement portion (56) extends (a) along at least a contiguous lower-securement axial segment (58) of the stent (20) and (b) circumferentially around a contiguous lower-securement circumferential portion (60) of the stent (20), which lower-securement axial segment (58) and lower-securement circumferential portion (60) include the one or more tether interfaces (50). The higher-securement portion (64) extends (a) along at least a contiguous higher-securement axial segment (65) of the stent (20) and (b) circumferentially around between 215 and 330 degrees of a circumference (C), at all circumferential locations other than those of the lower-securement circumferential portion (60). The stent (20) is shaped so as to define a plurality of outward protrusions (70) at respective circumferential locations (72) around the higher-securement portion (64), and not around (Continued)

the lower-securement portion (56). One or more tethers (34) are coupled to the one or more tether interfaces (50), respectively, and to one or more tissue anchors (30), respectively.

48 Claims, 13 Drawing Sheets

(51) Int. Cl.
A61F 2/848 (2013.01)
A61B 17/04 (2006.01)
A61F 2/24 (2006.01)
(52) U.S. Cl.
CPC ............... A61B 2017/0414 (2013.01); A61B 2017/0441 (2013.01); A61F 2/2418 (2013.01); A61F 2/2451 (2013.01); A61F 2/2487 (2013.01); A61F 2002/8486 (2013.01); A61F 2220/0008 (2013.01); A61F 2220/0016 (2013.01); A61F 2230/0069 (2013.01)
(58) Field of Classification Search
CPC ...... A61F 2002/8486; A61F 2220/0008; A61F 2220/0016; A61F 2230/0069; A61F 2002/91508; A61F 2002/91516; A61F 2002/91533; A61F 2002/91575; A61F 2002/9155; A61F 2002/91583; A61F 2/915
See application file for complete search history.

(56) References Cited

U.S. PATENT DOCUMENTS

| | | | |
|---|---|---|---|
| 4,423,525 A | 1/1984 | Vallana | |
| 4,444,207 A | 4/1984 | Robicsek | |
| 4,493,329 A | 1/1985 | Crawford et al. | |
| 4,532,926 A | 8/1985 | O'Holla | |
| 4,548,202 A | 10/1985 | Duncan | |
| 4,602,911 A | 7/1986 | Ahmadi et al. | |
| 4,625,727 A | 12/1986 | Leiboff | |
| 4,712,549 A | 12/1987 | Peters et al. | |
| 4,741,336 A | 5/1988 | Failla et al. | |
| 4,778,468 A | 10/1988 | Hunt et al. | |
| 4,808,157 A | 2/1989 | Coombs | |
| 4,853,986 A | 8/1989 | Allen | |
| 5,108,420 A | 4/1992 | Marks | |
| 5,330,521 A | 7/1994 | Cohen | |
| 5,336,233 A | 8/1994 | Chen | |
| 5,350,399 A | 9/1994 | Erlebacher et al. | |
| 5,450,860 A | 9/1995 | O'Connor | |
| 5,473,812 A | 12/1995 | Morris et al. | |
| 5,474,518 A | 12/1995 | Farrer-Velazquez | |
| 5,776,178 A | 7/1998 | Pohndorf et al. | |
| 5,792,400 A | 8/1998 | Talja et al. | |
| 5,843,120 A | 12/1998 | Israel | |
| 5,843,164 A | 12/1998 | Frantzen et al. | |
| 5,904,697 A | 5/1999 | Gifford et al. | |
| 5,948,000 A | 9/1999 | Larsen et al. | |
| 5,957,953 A | 9/1999 | DiPoto et al. | |
| 5,961,440 A | 10/1999 | Schweich, Jr. et al. | |
| 6,010,113 A | 1/2000 | Rotering | |
| 6,027,523 A | 2/2000 | Schmieding | |
| 6,045,497 A | 4/2000 | Schweich, Jr. et al. | |
| 6,050,936 A | 4/2000 | Schweich, Jr. et al. | |
| 6,077,214 A | 6/2000 | Mortier et al. | |
| 6,183,512 B1 | 2/2001 | Howanec et al. | |
| 6,193,734 B1 | 2/2001 | Bolduc et al. | |
| 6,206,913 B1 | 3/2001 | Yencho et al. | |
| 6,210,432 B1 | 4/2001 | Solem et al. | |
| 6,298,272 B1 | 10/2001 | Peterfeso et al. | |
| 6,299,635 B1 | 10/2001 | Frantzen | |
| 6,332,893 B1 | 12/2001 | Mortier et al. | |
| 6,338,738 B1 | 1/2002 | Bellotti et al. | |
| 6,402,780 B2 | 6/2002 | Williamson, IV et al. | |
| 6,402,781 B1 | 6/2002 | Langberg et al. | |
| 6,406,420 B1 | 6/2002 | McCarthy et al. | |
| 6,461,336 B1 | 10/2002 | Lane | |
| 6,533,810 B2 | 3/2003 | Hankh et al. | |
| 6,537,198 B1 | 3/2003 | Vidlund et al. | |
| 6,537,314 B2 | 3/2003 | Langberg et al. | |
| 6,575,976 B2 | 6/2003 | Grafton | |
| 6,585,766 B1 | 7/2003 | Huynh et al. | |
| 6,602,288 B1 | 8/2003 | Cosgrove et al. | |
| 6,613,078 B1 | 9/2003 | Barone | |
| 6,613,079 B1 | 9/2003 | Wolinsky | |
| 6,616,684 B1 | 9/2003 | Vidlund et al. | |
| 6,619,291 B2 | 9/2003 | Hlavka et al. | |
| 6,622,730 B2 | 9/2003 | Ekvall et al. | |
| 6,626,899 B2 | 9/2003 | Houser et al. | |
| 6,626,930 B1 | 9/2003 | Allen et al. | |
| 6,629,534 B1 | 10/2003 | St. Goar et al. | |
| 6,629,921 B1 | 10/2003 | Schweich, Jr. et al. | |
| 6,641,597 B2 | 11/2003 | Burkhart et al. | |
| 6,645,193 B2 | 11/2003 | Mangosong | |
| 6,702,846 B2 | 3/2004 | Mikus | |
| 6,709,456 B2 | 3/2004 | Langberg et al. | |
| 6,718,985 B2 | 4/2004 | Hlavka et al. | |
| 6,719,767 B1 | 4/2004 | Kimblad | |
| 6,723,038 B1 | 4/2004 | Schroeder et al. | |
| 6,730,118 B2 | 5/2004 | Spenser et al. | |
| 6,743,198 B1 | 6/2004 | Tihon | |
| 6,746,472 B2 | 6/2004 | Frazier et al. | |
| 6,764,510 B2 | 7/2004 | Vidlund et al. | |
| 6,776,754 B1 | 8/2004 | Wilk | |
| 6,797,001 B2 | 9/2004 | Mathis | |
| 6,810,882 B2 | 11/2004 | Langberg et al. | |
| 6,884,250 B2 | 4/2005 | Monassevitch | |
| 6,893,459 B1 | 5/2005 | Macoviak | |
| 6,908,478 B2 | 6/2005 | Alferness et al. | |
| 6,929,660 B1 | 8/2005 | Ainsworth et al. | |
| 6,989,028 B2 | 1/2006 | Lashinski et al. | |
| 6,997,951 B2 | 2/2006 | Solem et al. | |
| 7,011,682 B2 | 3/2006 | Lashinski et al. | |
| 7,018,406 B2 | 3/2006 | Seguin et al. | |
| 7,018,408 B2 | 3/2006 | Bailey et al. | |
| 7,037,290 B2 | 5/2006 | Gardeski et al. | |
| 7,041,097 B1 | 5/2006 | Webler | |
| 7,044,967 B1 | 5/2006 | Solem et al. | |
| 7,056,333 B2 | 6/2006 | Walshe | |
| 7,063,711 B1 | 6/2006 | Loshakove et al. | |
| 7,077,861 B2 | 7/2006 | Spence | |
| 7,083,628 B2 | 8/2006 | Bachman | |
| 7,087,064 B1 | 8/2006 | Hyde | |
| 7,094,244 B2 | 8/2006 | Schreck | |
| 7,101,395 B2 | 9/2006 | Tremulis et al. | |
| 7,101,396 B2 | 9/2006 | Artof et al. | |
| 7,112,219 B2 | 9/2006 | Vidlund et al. | |
| 7,125,421 B2 | 10/2006 | Tremulis et al. | |
| 7,144,363 B2 | 12/2006 | Pai et al. | |
| 7,159,593 B2 | 1/2007 | McCarthy et al. | |
| 7,166,127 B2 | 1/2007 | Spence et al. | |
| 7,169,187 B2 | 1/2007 | Datta | |
| 7,175,625 B2 | 2/2007 | Culbert | |
| 7,179,282 B2 | 2/2007 | Alferness et al. | |
| 7,186,262 B2 | 3/2007 | Saadat | |
| 7,189,199 B2 | 3/2007 | McCarthy et al. | |
| 7,192,442 B2 | 3/2007 | Solem et al. | |
| 7,192,443 B2 | 3/2007 | Solem et al. | |
| 7,198,646 B2 | 4/2007 | Figulla et al. | |
| 7,201,772 B2 | 4/2007 | Schwammenthal | |
| 7,211,107 B2 | 5/2007 | Bruckheime et al. | |
| 7,211,110 B2 | 5/2007 | Rowe et al. | |
| 7,241,257 B1 | 7/2007 | Ainsworth et al. | |
| 7,247,134 B2 | 7/2007 | Vidlund et al. | |
| 7,258,697 B1 * | 8/2007 | Cox | A61F 2/91 623/1.14 |
| 7,291,168 B2 | 11/2007 | Macoviak et al. | |
| 7,311,697 B2 | 12/2007 | Osborne | |
| 7,311,728 B2 | 12/2007 | Solem et al. | |
| 7,316,706 B2 | 1/2008 | Bloom et al. | |
| 7,316,710 B1 | 1/2008 | Cheng et al. | |
| 7,329,279 B2 | 2/2008 | Haug et al. | |

(56) References Cited

U.S. PATENT DOCUMENTS

| | | |
|---|---|---|
| 7,331,972 B1 | 2/2008 | Cox |
| 7,335,213 B1 | 2/2008 | Hyde et al. |
| 7,338,506 B2 | 3/2008 | Caro |
| 7,351,256 B2 | 4/2008 | Hojeibane |
| 7,371,244 B2 | 5/2008 | Chatlynne et al. |
| 7,374,573 B2 | 5/2008 | Gabbay |
| 7,381,210 B2 | 6/2008 | Zarbatany et al. |
| 7,381,220 B2 | 6/2008 | Macoviak et al. |
| 7,390,329 B2 | 6/2008 | Westra et al. |
| 7,431,692 B2 | 10/2008 | Zollinger et al. |
| 7,431,726 B2 | 10/2008 | Spence et al. |
| 7,485,143 B2 | 2/2009 | Webler et al. |
| 7,500,989 B2 | 3/2009 | Solem et al. |
| 7,503,931 B2 | 3/2009 | Kowalsky et al. |
| 7,510,575 B2 | 3/2009 | Spenser et al. |
| 7,527,646 B2 | 5/2009 | Randert et al. |
| 7,530,995 B2 | 5/2009 | Quijano et al. |
| 7,547,321 B2 | 6/2009 | Silvestri et al. |
| 7,549,983 B2 | 6/2009 | Roue et al. |
| 7,597,703 B2 | 10/2009 | Sater |
| 7,608,102 B2 | 10/2009 | Adams et al. |
| 7,618,449 B2 | 11/2009 | Tremulis et al. |
| 7,628,797 B2 | 12/2009 | Tieu et al. |
| 7,632,303 B1 | 12/2009 | Stalker et al. |
| 7,637,946 B2 | 12/2009 | Solem et al. |
| 7,666,204 B2 | 2/2010 | Thornton et al. |
| 7,695,512 B2 | 4/2010 | Lashinski et al. |
| 7,704,277 B2 | 4/2010 | Zakay et al. |
| 7,722,523 B2 | 5/2010 | Mortier et al. |
| 7,758,632 B2 | 7/2010 | Hojeibane et al. |
| 7,771,467 B2 | 8/2010 | Svensson |
| 7,780,726 B2 | 8/2010 | Seguin |
| 7,785,366 B2 | 8/2010 | Maurer et al. |
| 7,803,187 B2 | 9/2010 | Hauser |
| 7,806,910 B2 | 10/2010 | Anderson |
| 7,837,727 B2 | 11/2010 | Goetz et al. |
| 7,841,502 B2 | 11/2010 | Walberg et al. |
| 7,857,846 B2 | 12/2010 | Alferness et al. |
| 7,871,433 B2 | 1/2011 | Lattouf |
| 7,883,539 B2 | 2/2011 | Schweich, Jr. et al. |
| 7,892,214 B2 | 2/2011 | Kagan et al. |
| 7,947,207 B2 | 5/2011 | Mcniven et al. |
| 7,972,378 B2 | 7/2011 | Tabor et al. |
| 7,991,484 B1 | 8/2011 | Sengupta et al. |
| 7,992,567 B2 | 8/2011 | Hirotsuka |
| 7,993,368 B2 | 8/2011 | Gambale et al. |
| 7,993,397 B2 | 8/2011 | Lashinski et al. |
| 8,010,207 B2 | 8/2011 | Smits et al. |
| 8,025,495 B2 | 9/2011 | Hardert et al. |
| 8,029,518 B2 | 10/2011 | Goldfarb et al. |
| 8,052,592 B2 | 11/2011 | Goldfarb et al. |
| 8,075,616 B2 | 12/2011 | Solem et al. |
| 8,092,517 B2 | 1/2012 | Kalmann et al. |
| 8,092,520 B2 | 1/2012 | Quadri |
| 8,092,525 B2 | 1/2012 | Eliasen et al. |
| 8,100,820 B2 | 1/2012 | Hauser et al. |
| 8,108,054 B2 | 1/2012 | Helland |
| 8,109,996 B2 | 2/2012 | Stacchino et al. |
| 8,137,381 B2 | 3/2012 | Foerster et al. |
| 8,142,493 B2 | 3/2012 | Spence et al. |
| 8,142,495 B2 | 3/2012 | Hasenkam et al. |
| 8,147,542 B2 | 4/2012 | Maisano et al. |
| 8,157,810 B2 | 4/2012 | Case et al. |
| 8,197,441 B2 | 6/2012 | Webler et al. |
| 8,202,281 B2 | 6/2012 | Voss |
| 8,202,315 B2 | 6/2012 | Hlavka et al. |
| 8,216,302 B2 | 7/2012 | Wilson et al. |
| 8,226,707 B2 | 7/2012 | White |
| 8,236,013 B2 | 8/2012 | Chu |
| 8,236,049 B2 | 8/2012 | Rowe et al. |
| 8,252,005 B2 | 8/2012 | Findlay et al. |
| 8,262,567 B2 | 9/2012 | Sharp et al. |
| 8,262,724 B2 | 9/2012 | Seguin et al. |
| 8,262,725 B2 | 9/2012 | Subramanian |
| 8,267,981 B2 | 9/2012 | Boock et al. |
| 8,313,497 B2 | 11/2012 | Walberg et al. |
| 8,313,498 B2 | 11/2012 | Pantages et al. |
| 8,323,312 B2 | 12/2012 | Clark |
| 8,323,335 B2 | 12/2012 | Rowe et al. |
| 8,332,051 B2 | 12/2012 | Sommer et al. |
| 8,361,088 B2 | 1/2013 | McIntosh |
| 8,382,829 B1 | 2/2013 | Call et al. |
| 8,398,672 B2 | 3/2013 | Kleshinski et al. |
| 8,409,273 B2 | 4/2013 | Thornton et al. |
| 8,419,753 B2 | 4/2013 | Stafford |
| 8,430,893 B2 | 4/2013 | Ma |
| 8,449,606 B2 | 5/2013 | Eliasen et al. |
| 8,460,368 B2 | 6/2013 | Taylor et al. |
| 8,460,371 B2 | 6/2013 | Hlavka et al. |
| 8,475,525 B2 | 7/2013 | Maisano et al. |
| 8,480,691 B2 | 7/2013 | Dana et al. |
| 8,480,730 B2 | 7/2013 | Maurer et al. |
| 8,523,881 B2 | 9/2013 | Cabiri et al. |
| 8,524,132 B2 | 9/2013 | Von Oepen et al. |
| 8,529,621 B2 | 9/2013 | Alfieri et al. |
| 8,545,553 B2 | 10/2013 | Zipory et al. |
| 8,568,475 B2 | 10/2013 | Nguyen et al. |
| 8,568,476 B2 | 10/2013 | Rao et al. |
| 8,591,460 B2 | 11/2013 | Wilson et al. |
| 8,597,347 B2 | 12/2013 | Maurer et al. |
| 8,628,569 B2 | 1/2014 | Benichou et al. |
| 8,628,571 B1 | 1/2014 | Hacohen |
| 8,663,248 B2 | 3/2014 | Zung et al. |
| 8,685,080 B2 | 4/2014 | White |
| 8,685,083 B2 | 4/2014 | Perier et al. |
| 8,721,588 B2 | 5/2014 | Echarri et al. |
| 8,728,097 B1 | 5/2014 | Sugimoto et al. |
| 8,747,463 B2 | 6/2014 | Fogarty et al. |
| 8,753,357 B2 | 6/2014 | Roorda et al. |
| 8,753,373 B2 | 6/2014 | Chau et al. |
| 8,758,402 B2 | 6/2014 | Jenson et al. |
| 8,778,017 B2 | 7/2014 | Eliasen et al. |
| 8,784,481 B2 | 7/2014 | Alkhatib et al. |
| 8,790,394 B2 | 7/2014 | Miller et al. |
| 8,795,356 B2 | 8/2014 | Quadri et al. |
| 8,808,366 B2 | 8/2014 | Braido et al. |
| 8,808,368 B2 | 8/2014 | Maisano et al. |
| 8,845,723 B2 | 9/2014 | Spence et al. |
| 8,852,270 B2 | 10/2014 | Maurer et al. |
| 8,852,272 B2 | 10/2014 | Gross et al. |
| 8,858,594 B2 | 10/2014 | Clark |
| 8,858,623 B2 | 10/2014 | Miller et al. |
| 8,864,822 B2 | 10/2014 | Spence et al. |
| 8,870,949 B2 | 10/2014 | Rowe |
| 8,870,950 B2 | 10/2014 | Hacohen |
| 8,893,947 B2 | 11/2014 | Reynolds et al. |
| 8,911,461 B2 | 12/2014 | Traynor et al. |
| 8,926,691 B2 | 1/2015 | Chau et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,961,594 B2 | 2/2015 | Maisano et al. |
| 8,961,595 B2 | 2/2015 | Alkhatib |
| 8,961,596 B2 | 2/2015 | Maisano et al. |
| 8,968,335 B2 | 3/2015 | Robinson et al. |
| 8,968,336 B2 | 3/2015 | Conklin et al. |
| 8,968,395 B2 | 3/2015 | Hauser et al. |
| 8,979,922 B2 | 3/2015 | Jayasinghe et al. |
| 8,979,923 B2 | 3/2015 | Spence et al. |
| 9,005,273 B2 | 4/2015 | Salahieh et al. |
| 9,011,468 B2 | 4/2015 | Ketai et al. |
| 9,017,347 B2 | 4/2015 | Oba et al. |
| 9,034,032 B2 | 5/2015 | McLean et al. |
| 9,034,033 B2 | 5/2015 | McLean et al. |
| 9,078,652 B2 | 7/2015 | Conklin et al. |
| 9,084,676 B2 | 7/2015 | Chau et al. |
| 9,107,749 B2 | 8/2015 | Bobo et al. |
| 9,131,939 B1 | 9/2015 | Call et al. |
| 9,138,335 B2 | 9/2015 | Cartledge et al. |
| 9,180,005 B1 | 11/2015 | Lashinski et al. |
| 9,192,471 B2 | 11/2015 | Bolling |
| 9,211,203 B2 | 12/2015 | Pike et al. |
| 9,241,702 B2 | 1/2016 | Maisano et al. |
| 9,241,706 B2 | 1/2016 | Paraschac et al. |

(56) References Cited

U.S. PATENT DOCUMENTS

| | | |
|---|---|---|
| 9,259,218 B2 | 2/2016 | Robinson |
| 9,259,317 B2 | 2/2016 | Wilson et al. |
| 9,282,965 B2 | 3/2016 | Kokish |
| 9,289,282 B2 | 3/2016 | Olson et al. |
| 9,289,297 B2 | 3/2016 | Wilson et al. |
| 9,301,749 B2 | 4/2016 | Rowe et al. |
| 9,314,242 B2 | 4/2016 | Bachman |
| 9,326,870 B2 | 5/2016 | Berglund et al. |
| 9,358,111 B2 | 6/2016 | Spence et al. |
| 9,408,607 B2 | 8/2016 | Cartledge et al. |
| 9,474,605 B2 | 10/2016 | Rowe et al. |
| 2002/0013571 A1 | 1/2002 | Goldfarb et al. |
| 2002/0032481 A1 | 5/2002 | Gabbay |
| 2002/0082625 A1 | 6/2002 | Huxel et al. |
| 2002/0107564 A1 | 8/2002 | Cox et al. |
| 2002/0151961 A1 | 10/2002 | Lashinski et al. |
| 2002/0156517 A1 | 10/2002 | Perouse |
| 2002/0177904 A1 | 11/2002 | Huxel et al. |
| 2003/0033003 A1 | 2/2003 | Harrison et al. |
| 2003/0057156 A1 | 3/2003 | Peterson et al. |
| 2003/0083742 A1 | 5/2003 | Spence et al. |
| 2003/0093096 A1 | 5/2003 | McGuckin, Jr. et al. |
| 2003/0167071 A1 | 9/2003 | Martin et al. |
| 2003/0229350 A1 | 12/2003 | Kay |
| 2003/0236568 A1 | 12/2003 | Hojeibane et al. |
| 2004/0117009 A1 | 6/2004 | Cali et al. |
| 2004/0133274 A1 | 7/2004 | Webler et al. |
| 2004/0158314 A1 | 8/2004 | Hogendijk |
| 2004/0172046 A1 | 9/2004 | Hlavka et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0236419 A1 | 11/2004 | Milo |
| 2004/0260389 A1 | 12/2004 | Case et al. |
| 2005/0004668 A1 | 1/2005 | Aklog et al. |
| 2005/0016560 A1 | 1/2005 | Voughlohn |
| 2005/0021085 A1 | 1/2005 | Abrams et al. |
| 2005/0055089 A1 | 3/2005 | Macoviak et al. |
| 2005/0059997 A1 | 3/2005 | Bauman et al. |
| 2005/0075713 A1 | 4/2005 | Biancucci et al. |
| 2005/0075723 A1 | 4/2005 | Schroeder et al. |
| 2005/0080483 A1 | 4/2005 | Solem et al. |
| 2005/0090827 A1 | 4/2005 | Gedebou |
| 2005/0107812 A1 | 5/2005 | Starksen et al. |
| 2005/0107871 A1 | 5/2005 | Realyvasquez et al. |
| 2005/0113900 A1 | 5/2005 | Shiroff et al. |
| 2005/0125077 A1 | 6/2005 | Harmon et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0154448 A1 | 7/2005 | Cully et al. |
| 2005/0177180 A1 | 8/2005 | Kaganov et al. |
| 2005/0177224 A1 | 8/2005 | Fogarty et al. |
| 2005/0177228 A1 | 8/2005 | Solem |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Arayani |
| 2005/0251208 A1 | 11/2005 | Elmer et al. |
| 2005/0256532 A1 | 11/2005 | Nayak et al. |
| 2005/0273138 A1 | 12/2005 | To et al. |
| 2005/0283246 A1 | 12/2005 | Cauthen et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0052821 A1 | 3/2006 | Abbot et al. |
| 2006/0106420 A1 | 5/2006 | Dolan et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 | 8/2006 | Quinn |
| 2006/0200199 A1 | 9/2006 | Bonutti et al. |
| 2006/0229708 A1 | 10/2006 | Powell et al. |
| 2006/0241745 A1 | 10/2006 | Solem |
| 2006/0241748 A1 | 10/2006 | Lee et al. |
| 2006/0259135 A1 | 11/2006 | Navia et al. |
| 2006/0259137 A1 | 11/2006 | Artof et al. |
| 2006/0276871 A1 | 12/2006 | Lamson et al. |
| 2006/0282161 A1 | 12/2006 | Huynh et al. |
| 2007/0016287 A1 | 1/2007 | Cartledge |
| 2007/0016288 A1 | 1/2007 | Gurskis |
| 2007/0021781 A1 | 1/2007 | Jervis et al. |
| 2007/0032787 A1 | 2/2007 | Hassett et al. |
| 2007/0038221 A1 | 2/2007 | Fine et al. |
| 2007/0038296 A1 | 2/2007 | Navia |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055340 A1 | 3/2007 | Pryor |
| 2007/0060895 A1 | 3/2007 | Sibbitt et al. |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1 | 5/2007 | Davidson |
| 2007/0123936 A1 | 5/2007 | Goldin et al. |
| 2007/0162107 A1 | 7/2007 | Haug et al. |
| 2007/0168013 A1 | 7/2007 | Douglas |
| 2007/0185532 A1 | 8/2007 | Stone et al. |
| 2007/0198082 A1 | 8/2007 | Kapadia et al. |
| 2007/0203391 A1 | 8/2007 | Bloom et al. |
| 2007/0208389 A1 | 9/2007 | Amundson et al. |
| 2007/0219558 A1 | 9/2007 | Deutsch |
| 2007/0250160 A1 | 10/2007 | Rafiee |
| 2007/0265700 A1 | 11/2007 | Eliasen et al. |
| 2007/0270943 A1 | 11/2007 | Solem et al. |
| 2007/0276437 A1 | 11/2007 | Call et al. |
| 2007/0276467 A1 | 11/2007 | Kalmann |
| 2007/0282375 A1 | 12/2007 | Hindrichs et al. |
| 2007/0282429 A1 | 12/2007 | Hauser et al. |
| 2007/0288086 A1 | 12/2007 | Kalmann et al. |
| 2007/0288089 A1 | 12/2007 | Gurskis et al. |
| 2008/0003539 A1 | 1/2008 | Lundgren |
| 2008/0015617 A1 | 1/2008 | Harari et al. |
| 2008/0027268 A1 | 1/2008 | Buckner et al. |
| 2008/0027446 A1 | 1/2008 | Stone et al. |
| 2008/0027483 A1 | 1/2008 | Cartledge |
| 2008/0035160 A1 | 2/2008 | Woodson et al. |
| 2008/0058866 A1 | 3/2008 | Young et al. |
| 2008/0077231 A1 | 3/2008 | Heringes et al. |
| 2008/0097595 A1 | 4/2008 | Gabbay |
| 2008/0125861 A1 | 5/2008 | Webler et al. |
| 2008/0140116 A1 | 6/2008 | Bonutti |
| 2008/0140188 A1 | 6/2008 | Randert et al. |
| 2008/0167714 A1 | 7/2008 | St. Goar |
| 2008/0190989 A1 | 8/2008 | Crews et al. |
| 2008/0262598 A1 | 10/2008 | Elmaleh |
| 2008/0262609 A1 | 10/2008 | Gross et al. |
| 2008/0275469 A1 | 11/2008 | Fanton et al. |
| 2008/0281411 A1 | 11/2008 | Berreklouw et al. |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005863 A1 | 1/2009 | Goetz et al. |
| 2009/0043382 A1 | 2/2009 | Maurer et al. |
| 2009/0048668 A1 | 2/2009 | Wilson et al. |
| 2009/0082828 A1 | 3/2009 | Ostroff |
| 2009/0082847 A1 | 3/2009 | Zacharias et al. |
| 2009/0084386 A1 | 4/2009 | McClellan et al. |
| 2009/0099647 A1 | 4/2009 | Glimsdale et al. |
| 2009/0099649 A1 | 4/2009 | Chobotov et al. |
| 2009/0112052 A1 | 4/2009 | Lund et al. |
| 2009/0118776 A1 | 5/2009 | Kelsch et al. |
| 2009/0131849 A1 | 5/2009 | Maurer et al. |
| 2009/0132033 A1 | 5/2009 | Maurer et al. |
| 2009/0143808 A1 | 6/2009 | Houser |
| 2009/0149872 A1 | 6/2009 | Gross et al. |
| 2009/0171439 A1 | 7/2009 | Nis Sl |
| 2009/0216265 A1 | 8/2009 | DeVries |
| 2009/0240326 A1 | 9/2009 | Wilson et al. |

(56) References Cited

U.S. PATENT DOCUMENTS

| | | |
|---|---|---|
| 2009/0254103 A1 | 10/2009 | Deutsch et al. |
| 2009/0259307 A1 | 10/2009 | Gross et al. |
| 2009/0264991 A1 | 10/2009 | Paul et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0306622 A1 | 12/2009 | Machold et al. |
| 2009/0326648 A1 | 12/2009 | Machold et al. |
| 2010/0010620 A1* | 1/2010 | Weber ............... A61F 2/91 623/1.16 |
| 2010/0022948 A1 | 1/2010 | Wilson et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |
| 2010/0049293 A1 | 2/2010 | Zukowski et al. |
| 2010/0063520 A1 | 3/2010 | Bilotti |
| 2010/0063542 A1 | 3/2010 | Van der Burg et al. |
| 2010/0063586 A1 | 3/2010 | Hasenkam et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab |
| 2010/0174358 A1 | 7/2010 | Rabkin |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217309 A1 | 8/2010 | Hansen et al. |
| 2010/0217382 A1 | 8/2010 | Chau et al. |
| 2010/0228269 A1 | 9/2010 | Garrison et al. |
| 2010/0234935 A1 | 9/2010 | Bashiri |
| 2010/0249908 A1 | 9/2010 | Chau et al. |
| 2010/0249920 A1 | 9/2010 | Bolling et al. |
| 2010/0256743 A1 | 10/2010 | Hinchliffe et al. |
| 2010/0264192 A1 | 10/2010 | Marczyk |
| 2010/0268204 A1 | 10/2010 | Tieu et al. |
| 2010/0274276 A1* | 10/2010 | Chow ............... A61F 2/91 606/200 |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |
| 2010/0324668 A1 | 12/2010 | Maurer et al. |
| 2011/0004296 A1 | 1/2011 | Lutter et al. |
| 2011/0009818 A1 | 1/2011 | Goff |
| 2011/0011917 A1 | 1/2011 | Loulmet |
| 2011/0022164 A1 | 1/2011 | Quinn et al. |
| 2011/0029066 A1 | 2/2011 | Gilad |
| 2011/0029071 A1 | 2/2011 | Zlotnick et al. |
| 2011/0035000 A1 | 2/2011 | Nieminen et al. |
| 2011/0040366 A1 | 2/2011 | Goetz et al. |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0092993 A1 | 4/2011 | Jacobs |
| 2011/0093002 A1 | 4/2011 | Rucker et al. |
| 2011/0098732 A1 | 4/2011 | Jacobs |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0137397 A1 | 6/2011 | Chau et al. |
| 2011/0152998 A1 | 6/2011 | Berez et al. |
| 2011/0166636 A1 | 7/2011 | Rowe |
| 2011/0184510 A1* | 7/2011 | Maisano ............ A61B 17/0401 623/1.24 |
| 2011/0190879 A1 | 8/2011 | Tsukashima et al. |
| 2011/0208283 A1 | 8/2011 | Rust et al. |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251678 A1 | 10/2011 | Eidenschink |
| 2011/0264208 A1 | 10/2011 | Duffy et al. |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0143320 A1 | 1/2012 | Eliasen et al. |
| 2012/0029628 A1 | 2/2012 | Rowe |
| 2012/0035712 A1 | 2/2012 | Maisano |
| 2012/0083806 A1 | 4/2012 | Goertzen |
| 2012/0123531 A1 | 5/2012 | Tsukashima et al. |
| 2012/0130374 A1 | 5/2012 | Bouduban et al. |
| 2012/0130421 A1 | 5/2012 | Hafez et al. |
| 2012/0158053 A1 | 6/2012 | Paulos |
| 2012/0179244 A1 | 7/2012 | Schankereli et al. |
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |
| 2012/0283757 A1 | 11/2012 | Miller et al. |
| 2012/0296349 A1 | 11/2012 | Smith et al. |
| 2012/0310328 A1 | 12/2012 | Olson et al. |
| 2013/0030522 A1 | 1/2013 | Rowe et al. |
| 2013/0041459 A1 | 2/2013 | Wilson et al. |
| 2013/0046373 A1* | 2/2013 | Cartledge ............ A61F 2/966 623/1.11 |
| 2013/0053951 A1 | 2/2013 | Baliarda |
| 2013/0079873 A1 | 3/2013 | Migliazza et al. |
| 2013/0085529 A1 | 4/2013 | Housman |
| 2013/0096664 A1 | 4/2013 | Goetz et al. |
| 2013/0096672 A1 | 4/2013 | Reich et al. |
| 2013/0110230 A1 | 5/2013 | Solem |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0281760 A1 | 10/2013 | Farnan et al. |
| 2013/0296925 A1 | 11/2013 | Chanduszko et al. |
| 2013/0325110 A1 | 12/2013 | Khalil et al. |
| 2013/0331930 A1 | 12/2013 | Rowe et al. |
| 2014/0005778 A1 | 1/2014 | Buchbinder et al. |
| 2014/0018911 A1 | 1/2014 | Zhou et al. |
| 2014/0031864 A1 | 1/2014 | Jafari et al. |
| 2014/0031928 A1 | 1/2014 | Murphy et al. |
| 2014/0058405 A1 | 2/2014 | Foster |
| 2014/0066693 A1 | 3/2014 | Goldfarb et al. |
| 2014/0067054 A1 | 3/2014 | Chau et al. |
| 2014/0114390 A1 | 4/2014 | Tobis et al. |
| 2014/0121763 A1 | 5/2014 | Duffy et al. |
| 2014/0142689 A1 | 5/2014 | De Canniere et al. |
| 2014/0163690 A1 | 6/2014 | White |
| 2014/0200657 A1 | 7/2014 | Maurer et al. |
| 2014/0207231 A1 | 7/2014 | Hacohen et al. |
| 2014/0214159 A1 | 7/2014 | Vidlund et al. |
| 2014/0243894 A1 | 8/2014 | Groothuis et al. |
| 2014/0257475 A1 | 9/2014 | Gross et al. |
| 2014/0275757 A1 | 9/2014 | Goodwin et al. |
| 2014/0277390 A1 | 9/2014 | Ratz et al. |
| 2014/0277427 A1 | 9/2014 | Ratz et al. |
| 2014/0288639 A1 | 9/2014 | Gainor |
| 2014/0296962 A1 | 10/2014 | Cartledge et al. |
| 2014/0309730 A1 | 10/2014 | Alon et al. |
| 2014/0324164 A1 | 10/2014 | Gross et al. |
| 2014/0358224 A1 | 12/2014 | Tegels et al. |
| 2014/0371843 A1 | 12/2014 | Wilson et al. |
| 2014/0379006 A1 | 12/2014 | Sutherland et al. |
| 2014/0379074 A1 | 12/2014 | Spence et al. |
| 2014/0379076 A1 | 12/2014 | Vidlund et al. |
| 2015/0018940 A1 | 1/2015 | Quill et al. |
| 2015/0045879 A1 | 2/2015 | Longoria et al. |
| 2015/0051698 A1 | 2/2015 | Baliarda et al. |
| 2015/0066138 A1 | 3/2015 | Alexander et al. |
| 2015/0073545 A1 | 3/2015 | Braido |

(56) References Cited

U.S. PATENT DOCUMENTS

| | | |
|---|---|---|
| 2015/0094800 A1 | 4/2015 | Chawla |
| 2015/0094802 A1 | 4/2015 | Buchbinder et al. |
| 2015/0100116 A1 | 4/2015 | Mohl et al. |
| 2015/0119936 A1 | 4/2015 | Gilmore et al. |
| 2015/0127097 A1 | 5/2015 | Neumann et al. |
| 2015/0142049 A1 | 5/2015 | Delgado et al. |
| 2015/0142103 A1 | 5/2015 | Vidlund |
| 2015/0142105 A1 | 5/2015 | Bolling et al. |
| 2015/0157329 A1 | 6/2015 | Rudakov et al. |
| 2015/0182336 A1 | 7/2015 | Zipory et al. |
| 2015/0196693 A1 | 7/2015 | Lin |
| 2015/0223934 A1 | 8/2015 | Vidlund et al. |
| 2015/0250590 A1 | 9/2015 | Gries et al. |
| 2015/0272730 A1 | 10/2015 | Melnick et al. |
| 2015/0320414 A1 | 11/2015 | Conklin et al. |
| 2015/0351903 A1* | 12/2015 | Morriss ............. A61F 2/2418 623/2.11 |
| 2015/0351909 A1 | 12/2015 | Bobo et al. |
| 2015/0366666 A1 | 12/2015 | Khairkhahan et al. |
| 2016/0022417 A1 | 1/2016 | Karapetian et al. |
| 2016/0038285 A1 | 2/2016 | Glenn et al. |
| 2016/0081829 A1 | 3/2016 | Rowe |
| 2016/0120672 A1 | 5/2016 | Martin et al. |
| 2016/0128689 A1 | 5/2016 | Sutherland et al. |
| 2016/0157862 A1 | 6/2016 | Hernandez et al. |
| 2016/0174979 A1 | 6/2016 | Wei |
| 2016/0228246 A1 | 8/2016 | Zimmerman |
| 2016/0228252 A1 | 8/2016 | Keidar |
| 2016/0235526 A1 | 8/2016 | Lashinski et al. |
| 2016/0256269 A1 | 9/2016 | Cahalane et al. |
| 2016/0270776 A1 | 9/2016 | Miraki et al. |
| 2016/0270916 A1 | 9/2016 | Cahalane et al. |
| 2016/0287383 A1 | 10/2016 | Rowe |
| 2016/0287387 A1 | 10/2016 | Wei |

FOREIGN PATENT DOCUMENTS

| | | |
|---|---|---|
| EP | 1397176 | 3/2007 |
| EP | 1759663 | 3/2007 |
| EP | 1 836 971 | 9/2007 |
| EP | 1562522 | 12/2008 |
| EP | 1357843 | 5/2009 |
| EP | 1 968 491 | 7/2010 |
| EP | 1928357 | 11/2010 |
| EP | 1718249 | 4/2011 |
| EP | 2399549 | 3/2014 |
| EP | 1646332 | 6/2015 |
| EP | 2410948 | 7/2016 |
| EP | 2465568 | 8/2016 |
| EP | 2023858 | 10/2016 |
| WO | 1992/005093 | 4/1992 |
| WO | 1997/041778 | 11/1997 |
| WO | 2000/28923 | 5/2000 |
| WO | 2001/010306 | 2/2001 |
| WO | 2004/069055 A2 | 8/2004 |
| WO | 2004/082538 | 9/2004 |
| WO | 2005/021063 | 3/2005 |
| WO | 2005/058206 | 6/2005 |
| WO | 2005/102194 | 11/2005 |
| WO | 2006/019498 | 2/2006 |
| WO | 2006/034062 A1 | 3/2006 |
| WO | 2006/097931 | 9/2006 |
| WO | 2006/105008 | 10/2006 |
| WO | 2006/105009 | 10/2006 |
| WO | 2007/080595 | 7/2007 |
| WO | 2007/140309 | 12/2007 |
| WO | 2008/065044 | 6/2008 |
| WO | 2008/068756 | 6/2008 |
| WO | 2009/039400 | 3/2009 |
| WO | 2009/101617 | 8/2009 |
| WO | 2010/004546 | 1/2010 |
| WO | 2010/008549 | 1/2010 |
| WO | 2010/071494 | 6/2010 |
| WO | 2010/073246 | 7/2010 |
| WO | 2010/099032 | 9/2010 |
| WO | 2010/108079 | 9/2010 |
| WO | 2010/128502 | 11/2010 |
| WO | 2010/128503 | 11/2010 |
| WO | 2011/014496 | 2/2011 |
| WO | 2011/037891 | 3/2011 |
| WO | 2011/051942 | 5/2011 |
| WO | 2011/089601 | 7/2011 |
| WO | 2011/097355 | 8/2011 |
| WO | 2011/143263 | 11/2011 |
| WO | 2011/153408 | 12/2011 |
| WO | 2012/127309 | 9/2012 |
| WO | 2013/003228 | 1/2013 |
| WO | 2013/011502 | 1/2013 |
| WO | 2013/028145 | 2/2013 |
| WO | 2013/078497 | 6/2013 |
| WO | 2014/043527 | 3/2014 |
| WO | 2014/064694 | 5/2014 |
| WO | 2014/087402 | 6/2014 |
| WO | 2014/108903 A1 | 7/2014 |
| WO | 2014/141239 A1 | 9/2014 |
| WO | 2015/015497 | 2/2015 |
| WO | 2015/063580 A2 | 5/2015 |
| WO | 2015/193728 A2 | 12/2015 |
| WO | 2016/011275 | 1/2016 |
| WO | 2016/087934 A1 | 6/2016 |

OTHER PUBLICATIONS

Communication dated Jun. 23, 2016 from the State Intellectual Property Office of the P.R.C. in counterpart Application No. 201480028044.3.

Communication dated Sep. 5, 2016 from the State Intellectual Property Office of the P.R.C. in counterpart Application No. 201480028044.3.

An Office Action dated Sep. 16, 2016, which issued during the prosecution of U.S. Appl. No. 13/574,088.

Invitation to pay additional fees in PCT/IB2006/000840 dated Oct. 13, 2016.

An Interview Summary dated Dec. 5, 2016, which issued during the prosecution of U.S. Appl. No. 13/574,088.

An International Search Report and a Written Opinion both dated Apr. 15, 2016, which issued during the prosecution of Applicant's PCT/IB2015/002354.

An Office Action dated May 11, 2016, which issued during the prosecution of U.S. Appl. No. 13/574,088.

An International Search Report and a Written Opinion both dated Dec. 6, 2013, which issued during the prosecution of Applicant's PCT/IL2013/050470.

U.S. Appl. No. 61/783,224, filed Mar. 14, 2013.

Alfieri et al., "An effective technique to correct anterior mitral leaflet prolapse," J Card Surg 14(6):468-470 (1999).

Alfieri et al., "Novel suture device for beating heart mitral leaflet approximation," Annals of Thoracic Surgery 74:1488 1493 (2002).

Alfieri et al., "The double orifice technique in mitral valve repair: a simple solution for complex problems," Journal of Thoracic Cardiovascular Surgery 122:674-681 (2001).

Amplatzer Cardiac Plug Brochure (English Pages), AGA Medical Corporation, Plymouth, MN Copyright 2008-2011, downloaded Jan. 11, 2011.

Beale BS, "Surgical Repair of Collateral Ligament Injuries," presented at 63rd CVMA Convention, Halifax, Nova Scotia, Canada, Jul. 6-9, 2011.

Dentistry Today, "Implant Direct" product information page, Jun. 1, 2011, downloaded Dec. 10, 2012 from http://dentistrytoday.com/top25implant-i/5558-implant-direct.

Maisano et al., "The double-orifice technique as a standardized approach to treat mitral regurgitation due to severe myxomatous disease: surgical technique," European Journal of Cardio-thoracic Surgery 17 (2000) 201-205.

Shikhar Agarwal et al., "Interventional Cardiology Perspective of Functional Tricuspid Regurgitation," Circulatoin: Cardiovascular Interventions, pp. 565-573; Dec. 2009; vol. 2, Issue 6.

(56) References Cited

OTHER PUBLICATIONS

Smith & Nephew MINITAC™ TI 2.0 Suture Anchor Product Description, downloaded on Dec. 9, 2012 from http://global.smith-nephew.com/us/MINITAC_TI_2_SUTURE_ANCHR_3127.htm.
Second Notice of Allowance dated May 10, 2013, which issued during the prosecution of U.S. Appl. No. 12/692,061.
An Interview Summary dated Oct. 24, 2012, which issued during the prosecution of U.S. Appl. No. 12/692,061.
An Office Action dated Jul. 6, 2012, which issued during the prosecution of U.S. Appl. No. 12/692,061.
A Notice of Allowance dated Mar. 6, 2013, which issued during the prosecution of U.S. Appl. No. 12/692,061.
An International Search Report and a Written Opinion both dated May 19, 2011, which issued during the prosecution of Applicant's PCT/IL11/00064.
An International Search Report and a Written Opinion both dated Jan. 22, 2013, which issued during the prosecution of Applicant's PCT/IL2012/000282.
An Office Action dated Dec. 5, 2013, which issued during the prosecution of U.S. Appl. No. 13/485,145.
An International Search Report and a Written Opinion both dated Mar. 17, 2014, which issued during the prosecution of Applicant's PCT/IL2013/050937.
Invitation to pay additional fees in PCT/IL2014/050027 dated Apr. 4, 2014.
An International Search Report and a Written Opinion both dated May 28, 2014, which issued during the prosecution of Applicant's PCT/IL2014/050027.
U.S. Appl. No. 60/902,146, filed Feb. 16, 2007.
European Search Report dated Apr. 10, 2015, which issued during the prosecution of Applicant's European App No. 11734451.5.
European Search Report dated May 15, 2015, which issued during the prosecution of Applicant's European App No. 12814417.7.
An Office Action dated Sep. 14, 2015, which issued during the prosecution of U.S. Appl. No. 13/553,081.
An English Translation of an Office Action dated Jun. 30, 2014 which issued during the prosecution of Chinese Patent Application No. 201180015301.6.
An English Translation of an Office Action dated Jul. 7, 2015 which issued during the prosecution of Japanese Patent Application No. 2012-549463.
An Office Action dated Oct. 7, 2015, which issued during the prosecution of U.S. Appl. No. 13/574,088.
Invitation to Pay Additional Fees dated Apr. 20, 2015, which issued during the prosecution of Applicant's PCT/IB2014/002351.
An International Search Report and a Written Opinion both dated Jun. 10, 2015, which issued during the prosecution of Applicant's PCT/IB2014/002351.
An Office Action dated Feb. 2, 2015, which issued during the prosecution of U.S. Appl. No. 14/143,355.
An English Translation of an Office Action dated Feb. 10, 2015 which issued during the prosecution of Chinese Patent Application No. 201180015301.6.
An Office Action dated Feb. 25, 2015, which issued during the prosecution of U.S. Appl. No. 13/574,088.
Notice of Allowance dated Sep. 24, 2015, which issued during the prosecution of U.S. Appl. No. 14/143,355.
Notice of Allowance dated Dec. 4, 2015, which issued during the prosecution of U.S. Appl. No. 14/143,355.
An Office Action dated Jul. 7, 2014, which issued during the prosecution of U.S. Appl. No. 13/485,145.
An Office Action dated Sep. 25, 2014, which issued during the prosecution of U.S. Appl. No. 13/485,145.
An English Translation of an Office Action dated Oct. 28, 2014,which issued during the prosecution of Japanese Patent Application No. 2012-549463.
Notice of Allowance dated Dec. 9, 2014, which issued during the prosecution of U.S. Appl. No. No. 13/485,145.
An International Search Report and a Written Opinion both dated Jun. 30, 2014, which issued during the prosecution of Applicant's PCT/IL2014/050233.
An International Search Report and a Written Opinion both dated Jan. 8, 2016, which issued during the prosecution of Applicant's PCT/IB2015/001196.
Invitation to pay additional fees in PCT/IB2015/001196 dated Oct. 26, 2015.
Notice of Allowance dated Dec. 4, 2014, which issued during the prosecution of U.S. Appl. No. 13/188,175.
An Office Action dated Nov. 25, 2014, which issued during the prosecution of U.S. Appl. No. 13/553,081.
An Office Action dated Apr. 18, 2016, which issued during the prosecution of U.S. Appl. No. 14/584,286.
Spinal & Epidural Needles—downloaded on Feb. 18, 2016 from http://www.cothon.net/Anestesia_Obstetrica/Neuroaxial_needles.html.
Japanese Patent Office, Dec. 18, 2017 Office Action, JP Patent Application 563548/2015 (dated Dec. 26, 2017).

* cited by examiner

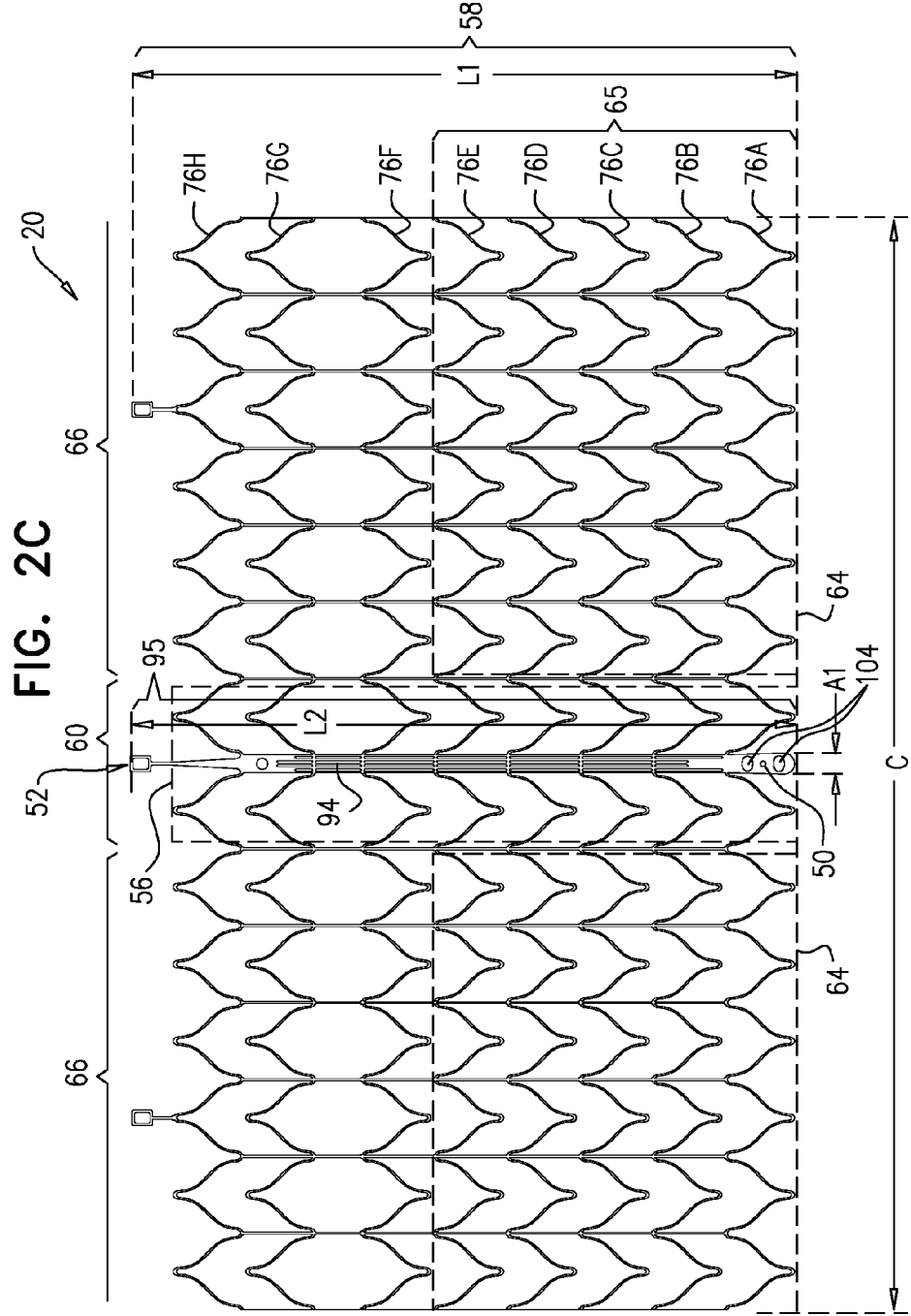

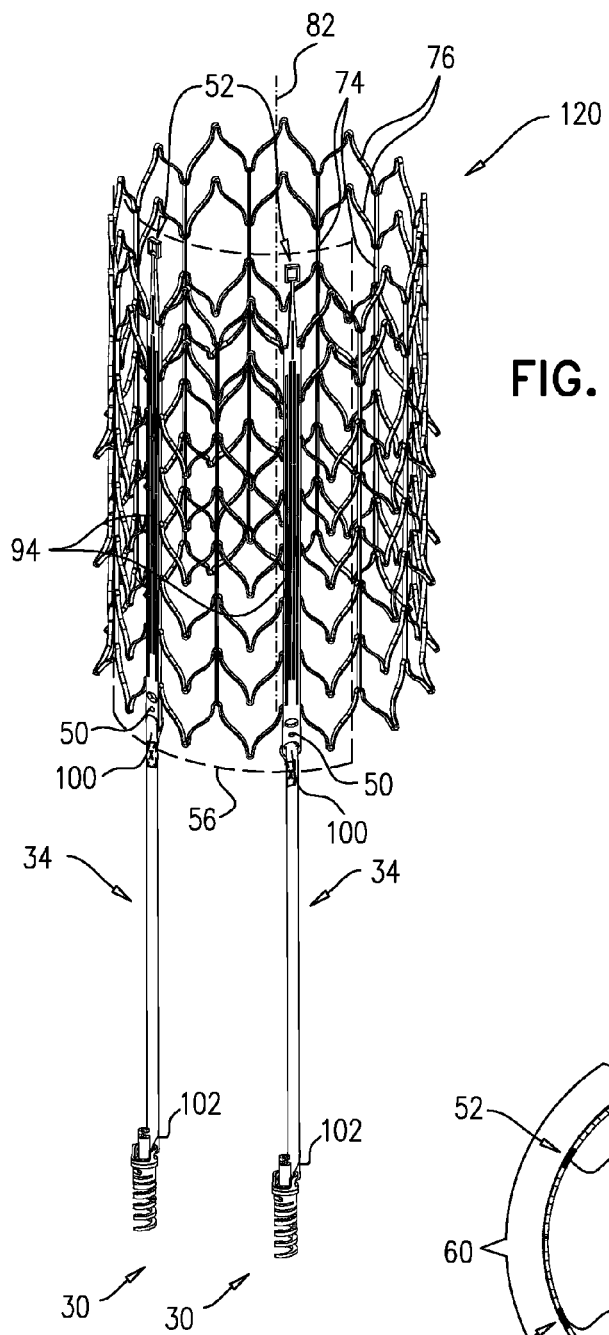
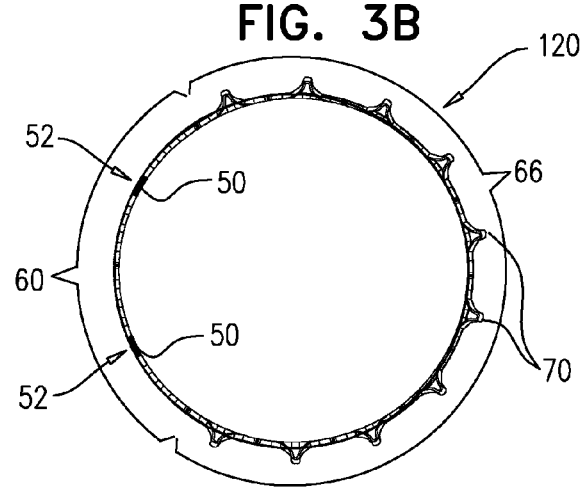
FIG. 3A
FIG. 3B

STENT WITH TETHER INTERFACE

CROSS-REFERENCE TO RELATED APPLICATIONS

The present application is the U.S. national stage of International Application PCT/IL2014/050233, filed Mar. 9, 2014, which claims priority from U.S. Provisional Application 61/783,224, filed Mar. 14, 2013, which is assigned to the assignee of the present application and is incorporated herein by reference.

FIELD OF THE APPLICATION

The present invention relates generally to stents, and specifically to stents for anchoring within body lumens.

BACKGROUND OF THE APPLICATION

Stents are used for various cardiovascular applications, such as to keep coronary vessels open, to act as grafts in abdominal aortic aneurisms ("AAAs"), to anchor vena cava filters, or to act as a frame for aortic valves. Stents are generally cylindrical, conical, or bottle shaped, and are designed to exert a radial force towards the vessel in which they are implanted. The resulting friction force provides securement of the stent to the vessel, thereby preventing migration of the stent after implantation. Techniques for increasing stent securement include providing hooks or barbs, shaping the stent into a truncated cone, and protruding the stent struts.

Functional tricuspid regurgitation (FTR) is governed by several pathophysiologic abnormalities such as tricuspid valve annular dilatation, annular shape, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in the United States. Of these, only 8,000 patients undergo tricuspid valve surgeries annually, most of them in conjunction with left heart valve surgeries.

SUMMARY OF THE APPLICATION

Some applications of the present invention provide an anchoring system, which comprises a radially-expandable stent, and typically one or more tissue anchors and one or more tethers that connect the stent to the one or more tissue anchors. The stent is configured to be implanted in a body lumen, such as a blood vessel. The stent typically lacks rotational symmetry, because some of the struts of a circumferential portion of the stent protrude outwardly and thereby define a polygonal shape, while the struts of another contiguous circumferential portion of the stent do not protrude outwardly and thereby define a cylindrical shape.

The circumferential portion with the outward protrusions exhibits higher securement forces with the wall of the body lumen than does the circumferential portion without the outward protrusions, thus allowing relative axial movement of the non-protruding circumferential portion while maintaining the stent as a whole secured in the body lumen. Such selective securement may relieve stresses in the stent frame resulting from cyclic loads applied to the stent (e.g., cyclic cardiac loads) at the one or more tether circumferential locations, thereby enabling higher fatigue endurance in the stent.

For some applications, when unconstrained in a radially-expanded state, the stent is generally tubular and shaped so as to define:

one or more tether interfaces at one or more tether circumferential locations, respectively, each of which tether interfaces extends circumferentially contiguously around less than 30 degrees of a circumference of the stent;

a lower-securement portion that extends (a) along at least a contiguous lower-securement axial segment of the stent and (b) circumferentially around a contiguous lower-securement circumferential portion of the stent, which lower-securement axial segment and lower-securement circumferential portion include the one or more tether interfaces;

a higher-securement portion that extends (a) along at least a contiguous higher-securement axial segment and (b) circumferentially around a higher-securement circumferential portion of the stent at all circumferential locations other than those of lower-securement circumferential portion. The higher-securement circumferential portion typically extends around between 215 and 330 degrees of the circumference of the stent (e.g., at least 270 degrees of the circumference); and a plurality of outward protrusions at respective outward circumferential locations around the higher-securement portion, and not around the lower-securement portion.

The outward protrusions of the higher-securement portion cause the higher-securement portion to apply greater securement forces against the body lumen wall than applied by the lower-securement portion, which lacks outward protrusions. Such selective securement allows relative axial reciprocating movement of struts of the lower-securement portion, while maintaining the stent as a whole secured in the body lumen. As described above, such selective securement may thus relieve stresses in the stent frame resulting from cyclic loads applied to the stent (e.g., cyclic cardiac loads) at the one or more tether circumferential locations, thereby enabling higher fatigue endurance in the stent, and reducing the risk of stent migration.

For some applications, the outward protrusions are rotationally-asymmetrically distributed around the circumference of the stent, when the stent is unconstrained in the radially-expanded state. Alternatively or additionally, for some applications, the outward protrusions are periodically distributed around the higher-securement circumferential portion, when the stent is unconstrained in the radially-expanded state. Typically, the outward protrusions are blunt, when the stent is unconstrained in the radially-expanded state. Thus, the securement is achieved using the stent struts themselves, without the need for additional features such as barbs or hooks which increase the crimp size of the stent without adding to radial stiffness. Additionally, because the outward protrusions are blunt, the implant may be less likely to cause body lumen dissection than if sharp anchoring elements were provided.

For some applications, struts of the stent are shaped so as to define a plurality of columnar struts and a plurality of circumferential stent meanders, coupled to the columnar struts at respective axial locations. Typically, each of the circumferential stent meanders is disposed around the entire circumference of the stent. A set of one or more of the circumferential stent meanders are shaped so as to define the outward protrusions at the respective outward circumferential locations around the higher-securement portion, when the stent is unconstrained in the radially-expanded state.

For some applications, when the stent is unconstrained in the radially-expanded state, at least one of the circumferential stent meanders is shaped so as to define (a) around the higher-securement portion, the outward protrusions (the circumferential stent meander may thus define a polygon if projected onto a plane perpendicular to a longitudinal axis of the stent), and (b) around the lower-securement portion, an arc of a circle if the circumferential stent meander is projected onto the plane perpendicular to the longitudinal axis of the stent. For some applications, exactly one, exactly two, exactly three, exactly four, or five or more of the circumferential stent meanders are thus shaped. In contrast, the other circumferential stent meanders do not define the outward protrusions, and thus define respective circles if projected onto the plane perpendicular to the longitudinal axis of the stent. The stent may be shaped to define other polygon-circular shape patterns (e.g., every x circumferential stent meanders may define outward protrusions, such as every second meander, or every third meander). For some applications, the lower-securement portion is generally shaped as a circumferential portion of a circular cylinder.

For some applications, the stent is shaped so as to define one or more (e.g., exactly one) tension-distributing elements, which (a) extend along at least a tether-distribution axial segment of the stent at the one or more tether circumferential locations, respectively, (b) define the one or more tether interfaces, respectively, and (c) are configured to distribute tension applied by the one or more tethers, respectively, along the tether-distribution axial segment.

There is therefore provided, in accordance with an application of the present invention, apparatus including:

a radially-expandable stent, which, when unconstrained in a radially-expanded state, is generally tubular and shaped so as to define:
  one or more tether interfaces at one or more tether circumferential locations, respectively, each of which tether interfaces extends circumferentially contiguously around less than 30 degrees of a circumference of the stent,
  a lower-securement portion that extends (a) along at least a contiguous lower-securement axial segment of the stent and (b) circumferentially around a contiguous lower-securement circumferential portion of the stent, which lower-securement axial segment and lower-securement circumferential portion include the one or more tether interfaces,
  a higher-securement portion that extends (a) along at least a contiguous higher-securement axial segment of the stent and (b) circumferentially around between 215 and 330 degrees of the circumference, at all circumferential locations other than those of the lower-securement circumferential portion, and
  a plurality of outward protrusions at respective circumferential locations around the higher-securement portion, and not around the lower-securement portion;
  one or more tissue anchors; and
  one or more tethers having respective first longitudinal portions that are coupled to the one or more tether interfaces, respectively, and respective second longitudinal portions, different from the respective first longitudinal portions, which are coupled to the one or more tissue anchors, respectively.

For some applications, the stent is shaped so as to define one or more tension-distributing elements, which (a) extend along at least a tension-distribution axial segment of the stent at the one or more tether circumferential locations, respectively, (b) define the one or more tether interfaces, respectively, and (c) are configured to distribute tension applied by the one or more tethers, respectively, along the tension-distribution axial segment of the stent. For some applications, the tension-distribution axial segment axially coincides with the lower-securement axial segment. For some applications, the one or more tension-distributing elements and the stent are fabricated from a single unit. For some applications, each of the one or more tension-distributing elements has a circumferential arc of between 1 and 15 degrees, when the stent is unconstrained in the radially-expanded state. For some applications, an axial length of each of the tension-distributing elements equals at least 15% of an axial length of the stent. For some applications, the axial length of the stent is between 20 and 120 mm, and the axial length of each of the tension-distributing elements is between 10 and 120 mm, when the stent is unconstrained in the radially-expanded state.

For some applications, the lower-securement axial segment of the stent extends along at least 30%, such as at least 100%, of an axial length of the stent, when the stent is unconstrained in the radially-expanded state.

For some applications, an interior of the stent defines a right circular cylindrical shape having a radius, and the outward protrusions extend radially outward from the cylindrical shape by a distance equal to between 5% and 25% of the radius, when the stent is unconstrained in the radially-expanded state.

For some applications, the one or more tether interfaces are shaped so as to define one or more openings, respectively, through which the one or more tethers are respectively coupled.

For some applications, each of the one or more tethers includes an element selected from the group consisting of: one or more metal struts, one or more metal wires, one or more flexible biocompatible textiles, and one or more flexible bands. For some applications, each of the one or more tethers has a length of between 20 and 120 mm.

For some applications, at least one of the one or more tissue anchors includes a helical tissue anchor.

For some applications, the stent is a first stent, and at least one of the one or more tissue anchors includes a second generally tubular stent.

For any of the applications described above, the one more tether interfaces may include exactly one tether interface at exactly one tether circumferential location, and the one or more tethers may include exactly one tether having a first longitudinal portion that is coupled to the tether interface. For some applications, the tether circumferential location is circumferentially centered in the lower-securement circumferential portion. For some applications, the higher-securement portion extends circumferentially around at least 270 degrees of the circumference of the stent, when the stent is unconstrained in the radially-expanded state. For some applications, the exactly one tether interface is shaped so as to define one or more openings through which the exactly one tether is coupled.

For any of the applications described above, the outward protrusions may be rotationally-asymmetrically distributed around the circumference of the stent, when the stent is unconstrained in the radially-expanded state.

For any of the applications described above, the outward protrusions may be periodically distributed around the higher-securement circumferential portion, when the stent is unconstrained in the radially-expanded state.

For any of the applications described above, the outward protrusions may be blunt, when the stent is unconstrained in the radially-expanded state. Alternatively, for any of the applications described above, the outward protrusions may be shaped so as to define respective barbs, when the stent is unconstrained in the radially-expanded state.

For any of the applications described above, the lower-securement portion may have a circumferential arc that equals at least 200% of an average of circumferential distances between circumferential midpoints of circumferentially-adjacent ones of the outward protrusions around the higher-securement portion, when the stent is unconstrained in the radially-expanded state.

For any of the applications described above, the stent may include a plurality of columnar struts and a plurality of circumferential stent meanders coupled to the columnar struts at respective axial locations, and one or more of the circumferential stent meanders may be shaped so as to define the outward protrusions at the respective circumferential locations around the higher-securement portion, when the stent is unconstrained in the radially-expanded state. For some applications, when the stent is unconstrained in the radially-expanded state, at least one of the circumferential stent meanders is shaped so as to define (a) around the higher-securement portion, the outward protrusions, and (b) around the lower-securement portion, an arc of a circle if the circumferential stent meander is projected onto a plane perpendicular to a longitudinal axis of the stent. For some applications, at least one of the circumferential stent meanders is shaped so as to define the outward protrusions around the higher-securement portion circumferentially between one or more circumferentially-adjacent pairs of the columnar struts, when the stent is unconstrained in the radially-expanded state. For some applications, at least one of the circumferential stent meanders is shaped so as to define a plurality of apices, at least some of which are shaped so as to define the outward protrusions, when the stent is unconstrained in the radially-expanded state. For some applications, respective radii of the columnar struts are measured between respective inner surfaces of the columnar struts and a central longitudinal axis of the stent, and an average of respective distances between the central longitudinal axis and respective most-outward surfaces of the protrusions equals between 105% and 125% of an average of the radii, when the stent is unconstrained in the radially-expanded state.

For any of the applications described above, the higher-securement portion may extend circumferentially around at least 270 degrees of the circumference of the stent, such as at least 300 degrees, when the stent is unconstrained in the radially-expanded state.

For any of the applications described above, the higher-securement portion may extend circumferentially around no more than 300 degrees of the circumference of the stent, when the stent is unconstrained in the radially-expanded state.

There is further provided, in accordance with an application of the present invention, apparatus including:
  a radially-expandable stent, which, when unconstrained in a radially-expanded state, is generally tubular and shaped so as to define:
    a plurality of tether interfaces at a plurality of tether circumferential locations, respectively, each of which tether interfaces extends circumferentially contiguously around less than 30 degrees of a circumference of the stent, a plurality of lower-securement portions that extend (a) along at least respective contiguous lower-securement axial segments of the stent and (b) circumferentially around respective contiguous lower-securement circumferential portions of the stent, wherein (i) each of the lower-securement axial segments includes one or more of the tether interfaces, (ii) each of the lower-securement circumferential portions includes one or more of the tether interfaces, and (iii) the lower-securement circumferential portions have respective circumferential arcs, each of which is between 30 and 90 degrees,
    a plurality of higher-securement portions that extend (a) along at least respective contiguous higher-securement axial segments of the stent and (b) circumferentially around respective higher-securement circumferential portions of the stent, collectively at all circumferential locations other than those of the lower-securement circumferential portions, wherein the lower- and the higher-securement portions alternate around the stent, and
    a plurality of outward protrusions at respective circumferential locations around the higher-securement portions, and not around the lower-securement portions, such that each of the higher-securement portions includes one or more of the outward protrusions;
  a plurality of tissue anchors; and
  a plurality of tethers having respective first longitudinal portions that are coupled to the plurality of tether interfaces, respectively, and respective second longitudinal portions, different from the respective first longitudinal portions, that are coupled the plurality of tissue anchors, respectively.

For some applications, the circumferential arcs of the lower-securement circumferential portions are equal to one another.

For some applications, the higher-securement circumferential portions have respective circumferential arcs that are equal to one another.

For some applications, the circumferential arcs of the lower-securement circumferential portions are equal to one another, and the higher-securement circumferential portions have respective circumferential arcs that are equal to one another.

For some applications, the stent is shaped so as to define a plurality of tension-distributing elements, which (a) extend along at least respective tension-distribution axial segments of the stent at the tether circumferential locations, respectively, (b) define the tether interfaces, respectively, and (c) are configured to distribute tension applied by the tethers, respectively, along the tension-distribution axial segments of the stent, respectively. For some applications, the tension-distribution axial segments axially coincide with the lower-securement axial segments, respectively. For some applications, the tension-distributing elements and the stent are fabricated from a single unit. For some applications, each of the tension-distributing elements has a circumferential arc of between 1 and 15 degrees, when the stent is unconstrained in the radially-expanded state. For some applications, an axial length of each of the tension-distributing elements equals at least 15% of an axial length of the stent. For some applications, the axial length of the stent is between 20 and 120 mm, and the axial length of each of the tension-distributing elements is between 10 and 120 mm, when the stent is unconstrained in the radially-expanded state.

For some applications, the lower-securement axial segment of the stent extends along at least 30%, such as at least 100%, of an axial length of the stent, when the stent is unconstrained in the radially-expanded state.

For some applications, an interior of the stent defines a right circular cylindrical shape having a radius, and the outward protrusions extend radially outward from the cylindrical shape by a distance equal to between 5% and 25% of the radius, when the stent is unconstrained in the radially-expanded state.

For some applications, the tether interfaces are shaped so as to define respective one or more openings through which the tethers are respectively coupled.

For some applications, each of the tethers includes an element selected from the group consisting of: one or more metal struts, one or more metal wires, one or more flexible biocompatible textiles, and one or more flexible bands. For some applications, each of the tethers has a length of between 20 and 120 mm.

For some applications, at least one of the tissue anchors includes a helical tissue anchor.

For some applications, the stent is a first stent, and at least one of the tissue anchors includes a second generally tubular stent.

For any of the applications described above, the stent, when unconstrained in the radially-expanded state, may be shaped so as to define a same number of the tether interfaces and the lower-securement portions. For some applications, the tether circumferential locations are circumferentially centered in the lower-securement portions, respectively.

For any of the applications described above, the outward protrusions may be rotationally-asymmetrically distributed around the circumference of the stent, when the stent is unconstrained in the radially-expanded state.

For any of the applications described above, the outward protrusions may be periodically distributed around each of the higher-securement circumferential portions, when the stent is unconstrained in the radially-expanded state.

For any of the applications described above, the outward protrusions may be blunt, when the stent is unconstrained in the radially-expanded state. Alternatively, for any of the applications described above, the outward protrusions may be shaped so as to define respective barbs, when the stent is unconstrained in the radially-expanded state.

For any of the applications described above, each of the circumferential arcs of the lower-securement circumferential portions may equal at least 200% of an average of circumferential distances between circumferential midpoints of circumferentially-adjacent ones of the outward protrusions around the higher-securement portions, when the stent is unconstrained in the radially-expanded state.

For any of the applications described above, the stent may include a plurality of columnar struts and a plurality of circumferential stent meanders coupled to the columnar struts at respective axial locations, and one or more of the circumferential stent meanders may be shaped so as to define the outward protrusions at the respective circumferential locations around the higher-securement portions, when the stent is unconstrained in the radially-expanded state. For some applications, when the stent is unconstrained in the radially-expanded state, at least one of the circumferential stent meanders is shaped so as to define (a) around the higher-securement portions, the outward protrusions, and (b) around the lower-securement portions, respective arcs of a circle if the circumferential stent meander is projected onto a plane perpendicular to a longitudinal axis of the stent. For some applications, at least one of the circumferential stent meanders is shaped so as to define the outward protrusions around the higher-securement portions circumferentially between one or more circumferentially-adjacent pairs of the columnar struts, when the stent is unconstrained in the radially-expanded state. For some applications, at least one of the circumferential stent meanders is shaped so as to define a plurality of apices, at least some of which are shaped so as to define the outward protrusions, when the stent is unconstrained in the radially-expanded state. For some applications, respective radii of the columnar struts are measured between respective inner surfaces of the columnar struts and a central longitudinal axis of the stent, and an average of respective distances between the central longitudinal axis and respective most-outward surfaces of the protrusions equals between 105% and 125% of an average of the radii, when the stent is unconstrained in the radially-expanded state.

The present invention will be more fully understood from the following detailed description of embodiments thereof, taken together with the drawings, in which:

BRIEF DESCRIPTION OF THE DRAWINGS

FIGS. 2A-D are schematic views of a stent of the anchoring system of FIG. 1, in accordance with an application of the present invention;

FIGS. 3A-B are schematic illustrations of another configuration of the anchoring system of FIG. 1, in accordance with an application of the present invention;

DETAILED DESCRIPTION OF APPLICATIONS

Figure 1:
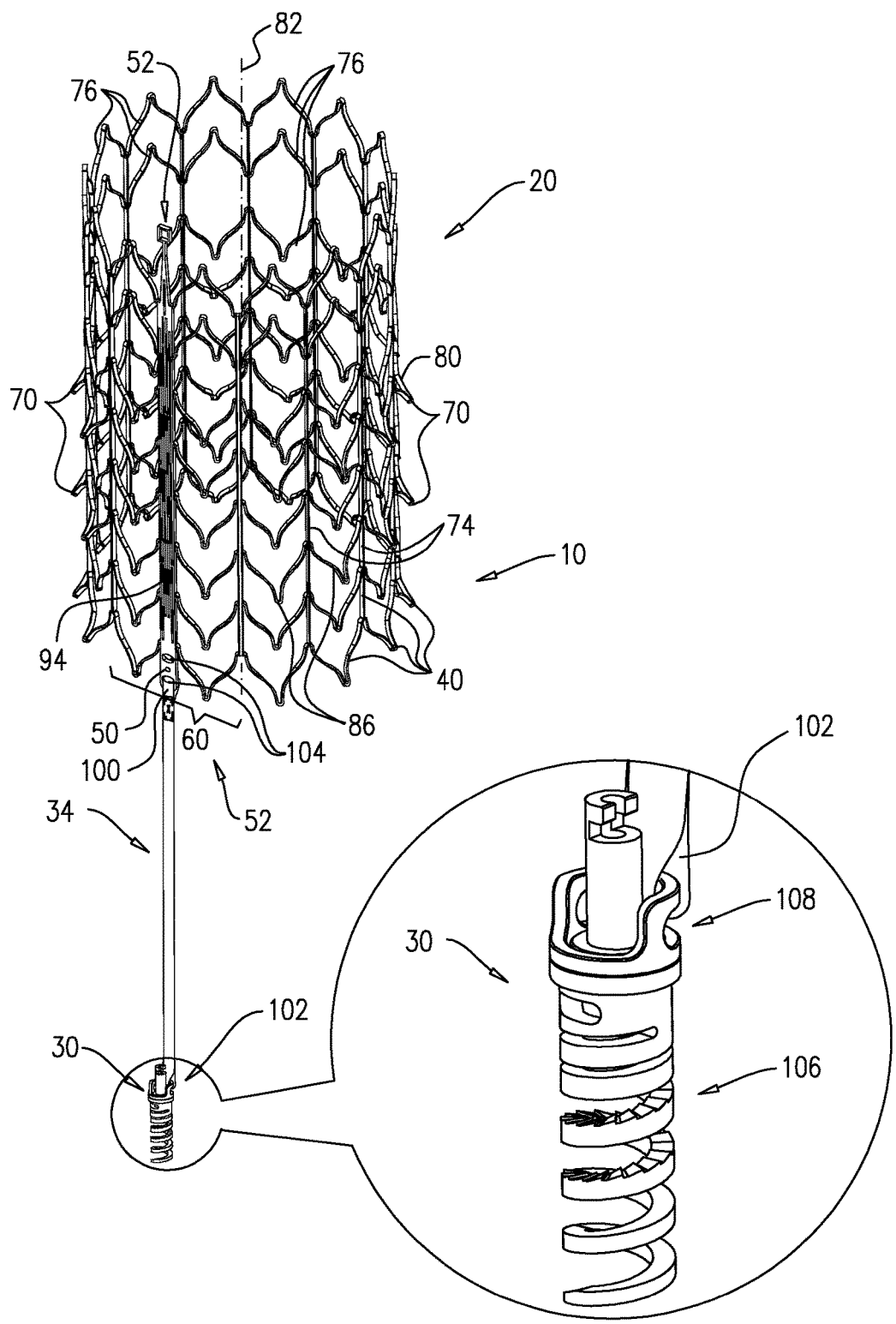
FIG. 1 is a schematic illustration of an anchoring system, in accordance with an application of the present invention.

FIG. 1 is a schematic illustration of an anchoring system 10, in accordance with an application of the present invention. Anchoring system 10 comprises a radially-expandable stent 20, and typically one or more tissue anchors 30 and one or more tethers 34 that connect the stent to the one or more tissue anchors. Stent 20 is configured to be implanted in a body lumen, such as a blood vessel. For some applications, anchoring system 10 is used for repairing an atrioventricular valve of a patient using tension, such as described hereinbelow with reference to FIGS. 5A-D. For these applications, one or more tissue anchors 30 are implantable in a vicinity of the atrioventricular valve, and stent 20 is expanded in a portion of a blood vessel, e.g., a superior vena cava, an inferior vena cava, a coronary sinus, or a hepatic vein, e.g., the left hepatic vein, the right hepatic vein, or the middle hepatic vein.

Figure 2A:
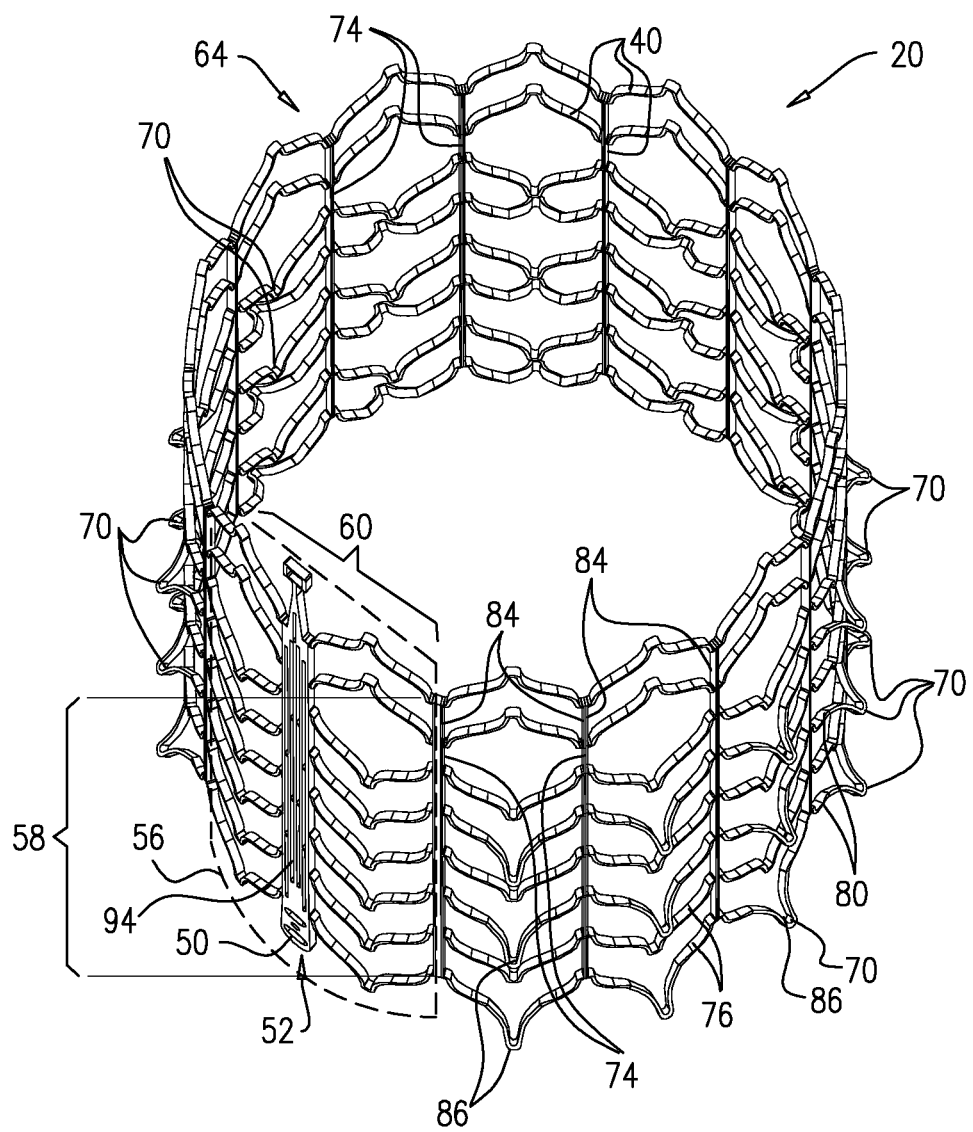
Figure 2B:
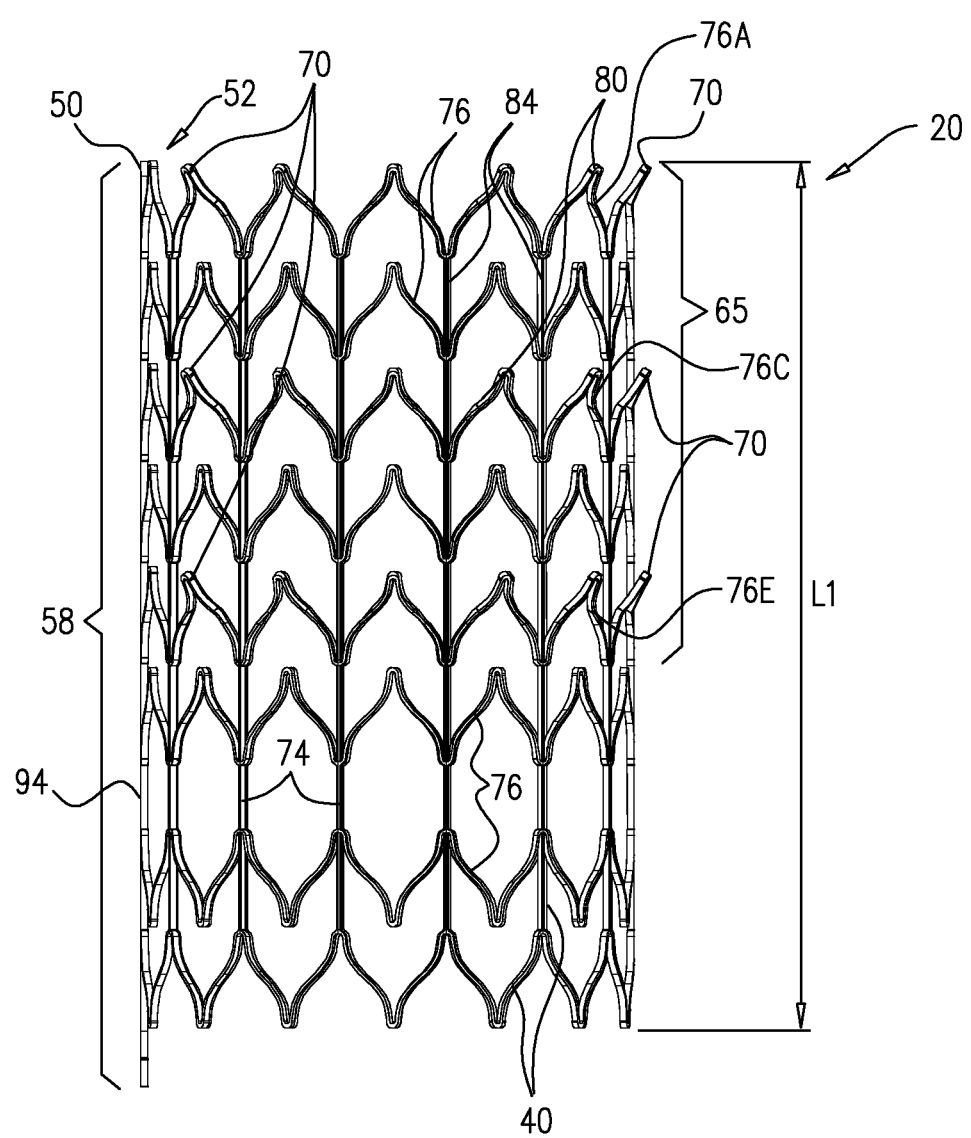
Figure 2D:
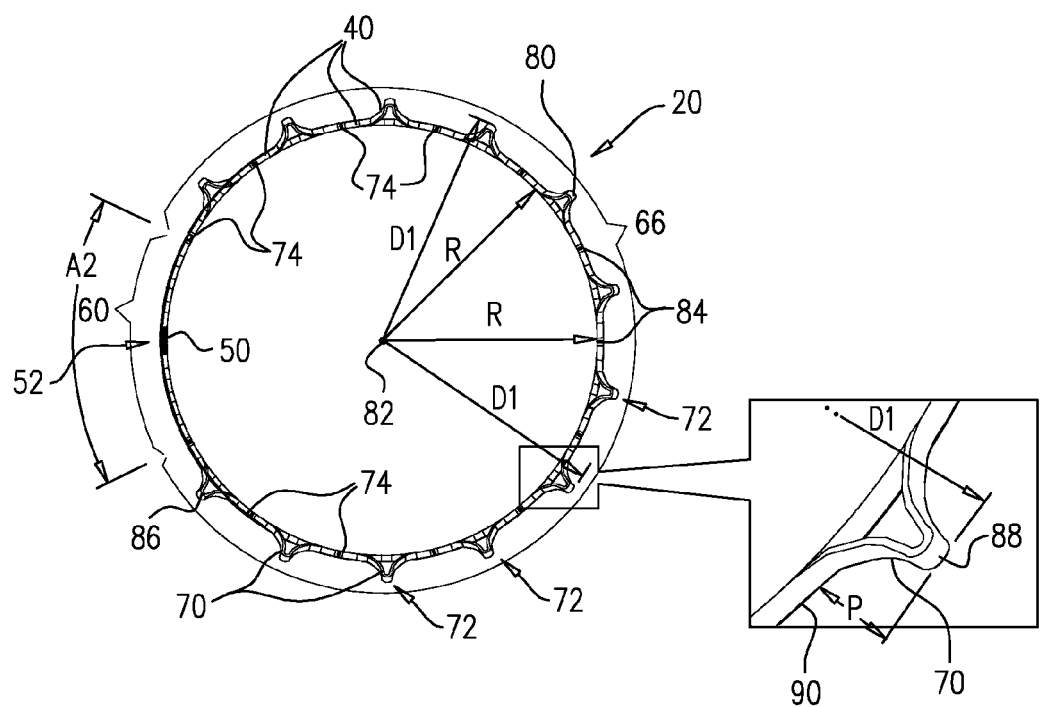

Reference is still made to FIG. 1, and is additionally made to FIGS. 2A-D, which are schematic views of stent 20, in accordance with an application of the present invention. FIGS. 2A-B are side-views of stent 20. For sake of illustration, FIG. 2C shows stent 20 in a flattened state, in which stent 20, when unconstrained in a radially-expanded state, has been cut longitudinally and flattened. It is noted that because of the particular flattened view in FIG. 2C, outward protrusions 70, described below, are not visible; these protrusions are in fact present. FIG. 2D is an end-view of stent 20.

Stent 20 typically comprises a plurality of interconnected superelastic metallic struts 40. Stent 20 may be manufactured by expanding a laser-slotted metallic tube, by chemically etching a flat sheet, by shaping a single wire, by assembling individual wire elements, or by any other method of construction known in the art. Stent 20 typically comprises a metal, such as a shape-memory alloy, e.g., Nitinol.

Stent 20, when unconstrained in a radially-expanded state (i.e., no forces are applied to the stent by a delivery tool, wall of a body vessel, or otherwise), such as shown in FIGS. 1 and 2A-D, is generally tubular and shaped so as to define:
  one or more tether interfaces 50 at one or more tether circumferential locations 52, respectively, each of which tether interfaces 50 extends circumferentially contiguously around less than 30 degrees of a circumference C of stent 20 (labeled in FIG. 2C). In the configuration shown in FIGS. 1 and 2A-D, stent 20 is shaped so as to define exactly one tether interface 50 at exactly one tether circumferential location 52, which extends circumferentially contiguously around less than 30 degrees of circumference C of stent 20;
  a lower-securement portion 56 that extends (a) along at least a contiguous lower-securement axial segment 58 of stent 20 (labeled in FIGS. 2A and 2C) and (b) circumferentially around a contiguous lower-securement circumferential portion 60 of stent 20, which lower-securement axial segment 58 and lower-securement circumferential portion 60 include the one or more tether interfaces 50 (e.g., exactly one tether interface 50, as shown in FIGS. 1 and 2A-D). Typically, lower-securement axial segment 58 extends along at least 30%, e.g., at least 70%, or 100% (as shown), of an axial length L1 of stent 20;
  a higher-securement portion 64 that extends (a) along at least a contiguous higher-securement axial segment 65 and (b) circumferentially around a higher-securement circumferential portion 66 of stent 20 at all circumferential locations other than those of lower-securement circumferential portion 60. Higher-securement circumferential portion 66 typically extends around at least 215 degrees of circumference C (e.g., at least 270 degrees, or at least 300 degrees), no more than 330 degrees of circumference C (e.g., no more than 300 degrees), and/or between 215 and 330 degrees of circumference C (e.g., between 270 and 330 degrees, such as between 300 and 330 degrees, or between 270 and 300 degrees); and
  a plurality of outward protrusions 70 at respective outward circumferential locations 72 around higher-securement portion 64, and not around lower-securement portion 56.

Outward protrusions 70 of higher-securement portion 64 cause higher-securement portion 64 to apply greater securement forces against the body lumen wall than applied by lower-securement portion 56, which lacks outward protrusions. Such selective securement allows relative axial reciprocating movement of struts 40 of lower-securement portion 56, while maintaining the stent as a whole secured in the body lumen. Such selective securement may thus relieve stresses in the stent frame resulting from cyclic loads applied to the stent (e.g., cyclic cardiac loads) at the one or more tether circumferential locations 52, thereby on the one hand enabling higher fatigue endurance in the stent, while on the other hand reducing the risk of stent migration.

Each of outward protrusions 70 is shaped so as to include a radially outward directional component. Optionally, each of the protrusions is shaped so as to additionally include an axial directional component, i.e., to point toward one end of the stent, typically pointing against the direction of axial force.

For some applications, as shown in FIGS. 1 and 2A-D, outward protrusions 70 are rotationally-asymmetrically distributed around circumference C of stent 20, when stent 20 is unconstrained in the radially-expanded state. Alternatively or additionally, for some applications, also as shown in FIGS. 1 and 2A-D, outward protrusions 70 are periodically distributed around higher-securement circumferential portion 66, when stent 20 is unconstrained in the radially-expanded state.

Typically, as shown in FIGS. 1 and 2A-D, outward protrusions 70 are blunt, when stent 20 is unconstrained in the radially-expanded state. Alternatively, outward protrusions 70 are shaped so as to define respective barbs 530, when stent 20 is unconstrained in the radially-expanded state, such as described hereinbelow with reference to FIGS. 7A-B.

For some applications, an axial length of lower-securement axial segment 58 is greater than an axial length of higher-securement axial segment 65, such as at least 10% greater, e.g., at least 30% or at least 50% greater. Typically, lower-securement axial segment 58 and higher-securement axial segment 65 partially axially overlap. For some applications, higher-securement axial segment 65 is aligned entirely axially within lower-securement axial segment 58 (although not circumferentially aligned therewith).

For some applications (configuration not shown), stent 20 includes a securement portion that does not axially overlap with either lower-securement axial segment 58 or higher-securement axial segment 65, and is typically located near the end of stent 20 opposite the end nearest the one or more tether interfaces 50.

For some applications, struts 40 are shaped so as to define a plurality of columnar struts 74 and a plurality of circumferential stent meanders 76 (defining a plurality of apices), coupled to columnar struts 74 at respective axial locations. Typically, each of circumferential stent meanders 76 is disposed around the entire circumference C of stent 20. For example, as perhaps may best seen in FIG. 2C, stent 20 may have eight circumferential stent meanders 76 and 14 columnar struts 74. It is to be understood that other configurations are possible, with any number of circumferential stent meanders 76. Typically, stent 20 comprises between three circumferential stent meanders 76 (for short stents, e.g., for a valve frame) and 20 circumferential stent meanders 76 (for long stents, e.g., for stent-grafts for treating abdominal aortic aneurisms ("AAAs")), and any number of columnar struts 74, typically between six and 20.

A set 80 of one or more of circumferential stent meanders 76 are shaped so as to define outward protrusions 70 at respective outward circumferential locations 72 around higher-securement portion 64, when stent 20 is unconstrained in the radially-expanded state. For some applications, each of circumferential stent meanders 76 of set 80 defines a number of outward protrusions 70 equal to between 20% and 100% of the total number of apices of the stent meander around the entire circumference C of the stent, such as between 50% and 90%, e.g., 86% (12/14). For some applications, each of circumferential stent meanders 76 of set 80 defines between 3 and 20 of outward protrusions 70, such as between 6 and 14 of outward protrusions 70, e.g., 12 of outward protrusions.

For some applications, when stent 20 is unconstrained in the radially-expanded state, at least one of circumferential stent meanders 76 is shaped so as to define:

around higher-securement portion 64, outward protrusions 70 (the circumferential stent meander may thus define a polygon if projected onto a plane perpendicular to a longitudinal axis 82 of stent 20); and around lower-securement portion 56, an arc of a circle if the circumferential stent meander is projected onto the plane perpendicular to longitudinal axis 82 of stent 20.

For some applications, exactly one, exactly two, exactly three (as shown), exactly four, or five or more of circumferential stent meanders 76 are thus shaped. For example, first, third, and fifth distal circumferential stent meanders 76A, 76C, and 76E include:

respective portions around higher-securement portion 64, which define outward protrusions 70 (and thus define respective polygons if projected onto the plane perpendicular to longitudinal axis 82 of stent 20), and respective portions around lower-securement portion 56, which do not define outward protrusions 70 (and thus define respective arcs of a circle if projected onto the plane perpendicular to longitudinal axis 82 of stent 20).

In contrast, second, fourth, sixth, seventh, and eighth circumferential stent meanders 76B, 76D, 76F, 76G, and 76H do not define outward protrusions 70, and thus define respective circles if projected onto the plane perpendicular to longitudinal axis 82 of stent 20. Stent 20 may be shaped to define other polygon-circular shape patterns (e.g., every x circumferential stent meanders 76 may define outward protrusions, such as every second meander, or every third meander). For some applications, lower-securement portion 56 is generally shaped as a circumferential portion of a circular cylinder. Such providing of lower-securement axial spaces between circumferential stent meanders may facilitate better fatigue resistance. In addition, the securement is provided by a plurality of circumferential stent meanders 76 at a respective plurality of axial locations, rather than only by a single row at one end of the stent, or single rows at each end of the stent, as in some conventional stents.

For some applications, when stent 20 is unconstrained in the radially-expanded state, at least one of circumferential stent meanders 76 is shaped so as to define outward protrusions 70 around higher-securement portion 64 circumferentially between one or more circumferentially-adjacent pairs 84 of columnar struts 74, such as between every circumferentially-adjacent pair of columnar struts 74 around higher-securement portion 64, as shown). For some applications, exactly one, exactly two, exactly three (as shown and described above), exactly four, or five or more of circumferential stent meanders 76 are thus shaped.

For some applications, outward protrusions 70 are cascaded around higher-securement portion 64.

For some applications, at least one of circumferential stent meanders 76 is shaped so as to define a plurality of apices 86, at least some of which are shaped so as to define outward protrusions 70, when stent 20 is unconstrained in the radially-expanded state.

For some applications, when stent 20 is unconstrained in the radially-expanded state, respective radii R of columnar struts 74 are measured between respective inner surfaces of columnar struts 74 and central longitudinal axis 82 of the stent. An average of respective distances D1 between respective most-outward surfaces 88 of outward protrusions 70 equals between 105% and 125% of an average of radii R. For applications in which stent 20 is shaped generally as a circular cylinder, radii R equal one another, and distances D1 typically equal one another. Alternatively or additionally, for some applications, when stent 20 is unconstrained in the radially-expanded state, outward protrusions 70 have a length P of at least 1 mm, no more than 5 mm, and/or between 1 and 5 mm, measured from an outer surface 90 of stent 20 other than at the protrusions. Further alternatively or additionally, for some applications, wherein an interior of stent 20 defines a right circular cylindrical shape having radius R, and outward protrusions 70 extend radially outward from the cylindrical shape by a distance equal to between 5% and 25% of radius R, when stent 20 is unconstrained in the radially-expanded state.

The dimensions of stent 20 may vary in order to fit the body lumen in which it is placed, according to the medical application. Typically, when unconstrained in the radially-expanded state, stent 20 has (a) an inner diameter D2 that equals about 10-30% larger than the inner diameter of the body lumen, and/or (b) axial length L1 that equals between 100% and 600% of inner diameter D2. For example, for applications in which stent 20 is configured to be implanted a vena cava for tethering anchor 30 at the tricuspid valve, such as described hereinbelow with reference to FIGS. 5A-D, (a) inner diameter D2 may be at least 25 mm, no more than 60 mm, and/or between 25 and 60 mm, (b) stent length L1 may be at least 25 mm, no more than 100 mm, and/or between 25 and 100 mm, and (c) protrusion length P may be 3 mm. For applications in which stent 20 is configured to be implanted in the abdominal aorta, (a) inner diameter D2 may be at least 30 mm, no more than 50 mm, and/or between 30 and 50 mm, (b) stent length L1 may be at least 50 mm, no more than 300 mm, and/or between 50 and 300 mm, and (c) protrusion length P may be 5 mm. For some applications, stent length L1 is at least 20 mm, no more than 120 mm, and/or between 20 and 120 mm, when stent 20 is unconstrained in the radially-expanded state.

Typically, inner diameter D2 is constant along the stent, i.e., the stent is not flared at either end.

For some applications, stent 20 is shaped so as to define one or more (e.g., exactly one) tension-distributing elements 94, which (a) extend along at least a tether-distribution axial segment 95 of stent 20 at the one or more tether circumferential locations 52, respectively, (b) define the one or more tether interfaces 50, respectively, and (c) are configured to distribute tension applied by the one or more tethers 34, respectively, along tether-distribution axial segment 95. For some applications, as shown, tether-distribution axial segment 95 axially coincides with lower-securement axial segment 58. Optionally, the one or more tension-distributing elements 94 and stent 20 are fabricated from a single unit.

For some applications, each of the one or more tension-distributing elements 94 has a circumferential arc A1 (labeled in FIG. 2C) of at least 1 degree, no more than 15 degrees, and/or between 1 and 15 degrees when stent 20 is unconstrained in the radially-expanded state. For some applications, an axial length L2 of each of tension-distributing elements 94 equals at least 15% of axial length L1 of stent 20, such as at least 75% of axial length L1 of stent 20. For some applications, such as when stent length L1 is at least 20 mm, no more than 120 mm, and/or between 20 and 120 mm, axial length L2 of each of tension-distributing elements 94 is at least 10 mm, no more than 120, and/or between 10 and 120 mm, when stent 20 is unconstrained in the radially-expanded state.

For some applications, lower-securement portion 56 has a circumferential arc A2 that equals at least 150% (e.g., at least 200%) of an average of circumferential distances D3 between circumferential midpoints 96 of circumferentially-adjacent ones 98 of outward protrusions 70 around higher-securement portion 64, when stent 20 is unconstrained in the radially-expanded state.

Reference is again made to FIG. 1. The one or more tethers 34 have respective first longitudinal portions 100 that are coupled to the one or more tether interfaces 50, respectively, and respective second longitudinal portions 102, different from respective first longitudinal portions 100, which are coupled to the one or more tissue anchors 30, respectively. For some applications, the one or more tether interfaces 50 are shaped so as to define one or more openings 104, respectively, through which the one or more tethers 34 are respectively coupled.

For some applications, each of the one or more tethers 34 comprises an element selected from the group consisting of: one or more metal struts, one or more metal wires, one or more flexible biocompatible textiles, and one or more flexible bands. For some applications, each of the one or more tethers 34 has a length of at least 20 mm, no more than 120 mm, and/or between 20 and 120 mm.

For some applications, at least one of the one or more tissue anchors 30 comprises a helical tissue anchor. For some applications, the helical tissue anchor comprises a generally helical shaftless tissue-coupling element 106 and, typically, a proximal head 108. For some applications, such as described in U.S. Provisional Application 61/750,427, filed Jan. 9, 2013, which is assigned to the assignee of the present application and is incorporated herein by reference, helical tissue-coupling element 106 has (a) a first axial thickness along a first axial portion of a shaftless helical portion of the helical tissue-coupling element, and (b) a second axial thickness along a second axial portion of the shaftless helical portion more distal than the first axial portion. The second axial thickness is greater than the first axial thickness. The first and second axial thicknesses are measured along a longitudinal axis of the helical tissue-coupling element.

Alternatively or additionally, the helical tissue-coupling element has (a) a first axial yield strength along the first axial portion, and (b) a second axial yield strength along the second axial portion (more distal than the first axial portion). The second axial yield strength is greater than the first axial yield strength. Further alternatively or additionally, the helical tissue-coupling element has (a) a first axial stiffness along the first axial portion, and (b) a second axial stiffness along the second axial portion (more distal than the first axial portion). The second axial stiffness is greater than the first axial stiffness.

For some applications, such as described in the above-mentioned '427 application, the helical tissue-coupling element 106 is shaped so as to define (a) a first surface along a first axial surface characteristic portion of the shaftless helical portion of the helical tissue-coupling element, which first surface has a first surface characteristic, and (b) a second surface along a second axial surface characteristic portion of the shaftless helical portion different from the first axial surface characteristic portion. The second surface has a second surface characteristic that is configured to inhibit rotation of the helical tissue-coupling element to a greater extent than does the first surface characteristic. The first surface characteristic may, for example, be a high level of smoothness.

For some applications, stent 20 is a first stent, and at least one of the one or more tissue anchors 30 comprises a second generally tubular stent. A similar two-stent configuration (albeit without the stent configurations described herein) is shown, for example, in FIG. 4C of PCT Publication WO 2013/011502, which is incorporated herein by reference. For some applications, the second stent is expanded in a portion of a second blood vessel of the patient, e.g., the superior vena cava, the inferior vena cava, the coronary sinus, or a hepatic vein, e.g., the left hepatic vein, the right hepatic vein, or the middle hepatic vein.

For some applications, as shown in FIGS. 1 and 2A-D, the one more tether interfaces 50 comprise exactly one tether interface 50 at exactly one tether circumferential location 52, and the one or more tethers 34 comprise exactly one tether 34 having a first longitudinal portion that is coupled to the tether interface. In some of these applications, higher-securement portion 64 extends circumferentially around at least 270 degrees of circumference C of stent 20, when stent 20 is unconstrained in the radially-expanded state.

For some applications, tether circumferential location 52 is circumferentially centered in lower-securement circumferential portion 60, as shown in FIGS. 2A-D. Alternatively, tether circumferential location 52 is not circumferentially centered in lower-securement circumferential portion 60 (configuration not shown). For some applications, the exactly one tether interface is shaped so as to define the one or more openings 104 through which the exactly one tether is coupled.

Reference is now made to FIGS. 3A-B, which are schematic illustrations of another configuration of anchoring system 10, in accordance with an application of the present invention. In this configuration, anchoring system 10 comprises a radially-expandable stent 120, which is one configuration of stent 20 described hereinabove with reference to FIGS. 1 and 2A-D. As mentioned above, anchoring system 10 typically comprises one or more tissue anchors 30 and one or more tethers 34 that connect the stent to the one or more tissue anchors. Also as mentioned above, stent 20, when unconstrained in the radially-expanded state (i.e., no forces are applied to the stent by a delivery tool, wall of a body vessel, or otherwise), is shaped so as to define one or more tether interfaces 50 at one or more tether circumferential locations 52, respectively.

In the configuration shown in FIGS. 3A-B, anchoring system comprises two tissue anchors 30 and two tethers 34 that connect stent 120 to the two tissue anchors, respectively. Stent 120 is shaped so as to define two tether interfaces 50 at two tether circumferential locations 52, respectively, each of which extends circumferentially contiguously around less than 30 degrees of circumference C of stent 20. Two tethers 34 have respective first longitudinal portions 100 that are coupled to two tether interfaces 50, respectively, and two respective second longitudinal portions 102, different from respective first longitudinal portions 100, which are coupled to two tissue anchors 30, respectively.

This configuration may be useful for applying tension to two sites to which the two anchors are coupled, such as two sites of the tricuspid valve. For example, this configuration may be used in combination with the anchor placement described with reference to, and shown in, FIG. 2B and/or FIG. 3B of above-mentioned PCT Publication WO 2013/011502, mutatis mutandis.

Figure 4A:
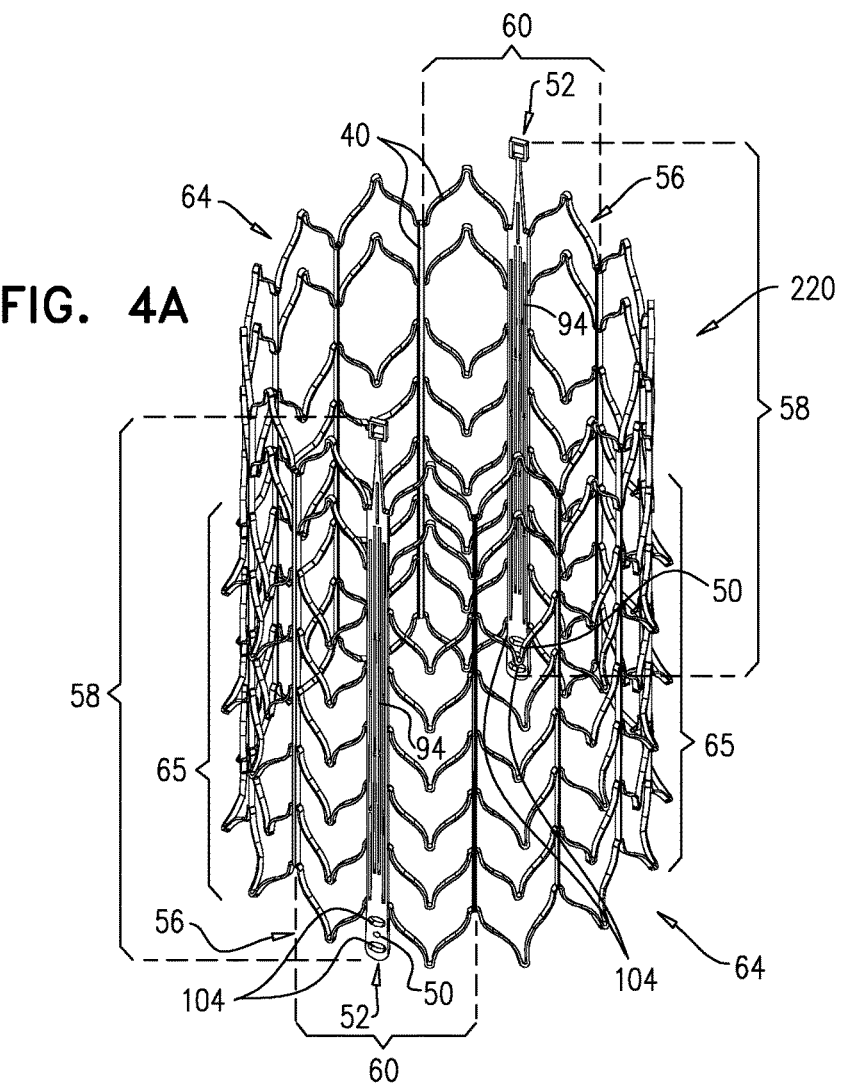
FIGS. 4A-B are schematic illustrations of another radially-expandable stent, in accordance with an application of the present invention.
Figure 4B:
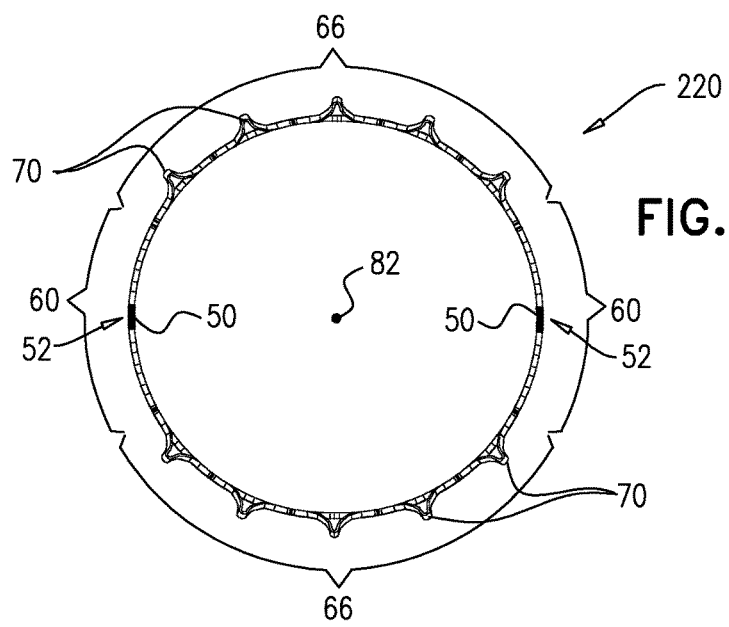

Reference is now made to FIGS. 4A-B, which are schematic illustrations of another radially-expandable stent 220, in accordance with an application of the present invention. FIGS. 4A and 4B are side- and end-views of stent 220, respectively. In this configuration, anchoring system 10 comprises radially-expandable stent 220, a plurality (e.g., two) of tissue anchors 30 and a plurality (e.g., two) of tethers 34 that connect the stent to the one or more tissue anchors.

Other than as described below, stent 220 may have any of the features of stent 20, described hereinabove with reference to FIGS. 1 and 2A-D.

Stent 220 typically comprises a plurality of interconnected superelastic metallic struts 40, and may be manufactured as described hereinabove regarding stent 20. Stent 220, when unconstrained in a radially-expanded state (i.e., no forces are applied to the stent by a delivery tool, wall of a body vessel, or otherwise), such as shown in FIGS. 4A-D, is generally tubular and shaped so as to define:

- a plurality of tether interfaces 50 at a plurality of tether circumferential locations 52, respectively, each of which tether interfaces 50 extends circumferentially contiguously around less than 30 degrees of a circumference of stent 220. In the configuration shown in FIGS. 4A-B, stent 220 is shaped so as to define two tether interfaces 50 at two tether interface locations 52;
- a plurality of lower-securement portions 56 that extend (a) along at least respective contiguous lower-securement axial segments 58 of stent 220 and (b) circumferentially around respective contiguous lower-securement circumferential portions 60 of stent 220. Each of lower-securement axial segments 58 includes one or more of tether interfaces 50 (e.g., exactly one of tether interfaces 50, as shown in FIGS. 4A-B). Each of lower-securement circumferential portions 60 includes one or more of tether interfaces 50 (e.g., exactly one of tether interfaces 50, as shown in FIGS. 4A-B). Lower-securement portions 56 have respective circumferential arcs, each of which typically is between 30 and 90 degrees;
- a plurality of higher-securement portions 64 that extend (a) along at least respective contiguous higher-securement axial segments 65 and (b) circumferentially around respective higher-securement circumferential portions 66 of stent 220, collectively at all circumferential locations other than those lower-securement circumferential portions 60. Lower- and higher-securement portions 56 and 64 alternate around stent 220 (such that there are an equal number of lower- and higher-securement portions 56 and 64); and
- a plurality of outward protrusions 70 at respective outward circumferential locations 72 around higher-securement portions 64, and not around lower-securement portions 56, such that each of higher-securement portions 64 includes one or more of outward protrusions 70.

Outward protrusions 70 of higher-securement portion 64 cause higher-securement portion 64 to apply greater securement forces against the body lumen wall than applied by lower-securement portion 56, which lacks outward protrusions. Such selective securement allows relative axial reciprocating movement of struts 40 of lower-securement portion 56, while maintaining the stent as a whole secured in the body lumen. Such selective securement may thus relieve stresses in the stent frame resulting from cyclic loads applied to the stent (e.g., cyclic cardiac loads) at tether circumferential locations 52, thereby enabling higher fatigue endurance in the stent.

For some applications, the circumferential arcs of lower-securement circumferential portions 60 are equal to one another. Alternatively or additionally, for some applications, higher-securement circumferential portions 66 have respective circumferential arcs that are equal to one another.

For some applications, stent 220, when unconstrained in the radially-expanded state, is shaped so as to define a same number of tether interfaces 50 and lower-securement portions 56. For some applications, tether circumferential locations 52 are circumferentially centered in lower-securement circumferential portions 60, respectively, as shown in FIGS. 4A-B. Alternatively, tether circumferential locations 52 are not circumferentially centered in lower-securement circumferential portions 60, respectively (configuration not shown).

For some applications, struts 40 are shaped so as to define the plurality of columnar struts 74 and the plurality of circumferential stent meanders 76 coupled to columnar struts 74 at respective axial locations. Typically, each of circumferential stent meanders 76 is disposed around the entire circumference of stent 220. For some applications, when stent 220 is unconstrained in the radially-expanded state, at least one of circumferential stent meanders 76 is shaped so as to define (a) around higher-securement portions 64, outward protrusions 70, and (b) around lower-securement portions 56, respective arcs of a circle if the circumferential stent meander is projected onto a plane perpendicular to longitudinal axis 82 of stent 220.

As mentioned above, stent 220 may have any of the features of stent 20, described hereinabove with reference to FIGS. 1 and 2A-D. Such features include, but are not limited to, (a) a plurality of tension-distributing elements 94, which are configured to distribute tension applied by tethers 34, respectively, along the axial portion of stent 220, (b) the rotationally asymmetric distribution of outward protrusions 70 around the circumference of stent 220, when stent 220 is unconstrained in the radially-expanded state, and (c) the periodic distribution of outward protrusions 70 around each of higher-securement circumferential portions 66, when stent 220 is unconstrained in the radially-expanded state.

The configuration described with reference to FIGS. 4A-B may be useful for applying tension to two sites to which the two anchors are coupled, such as two sites of the tricuspid valve. For example, this configuration may be used in combination with the anchor placement described with reference to, and shown in, FIG. 2B and/or FIG. 3B of above-mentioned PCT Publication WO 2013/011502, mutatis mutandis.

Reference is now made to FIGS. 5A-D, which are schematic illustrations of an exemplary deployment of anchoring system 10 for repairing a tricuspid valve 304 of a heart 302 of a patient, in accordance with some applications of the present invention. Although FIGS. 5A-D show the deployment of stent 20, described hereinabove with reference to FIGS. 1 and 2A-D, the same techniques, mutatis mutandis, may be used for deploying stent 120, described hereinabove with reference to FIGS. 3A-B, stent 220, described hereinabove with reference to FIGS. 4A-B, and stent 420, described hereinbelow with reference to FIGS. 6A-B.

System 10 is used for adjusting a distance between first and second implantation sites by pulling to apply tension to or relaxing tether 34 and/or by applying tension to at least one of tissue anchor 30 and stent 20. Responsively, a distance between the leaflets of tricuspid valve 304 is adjusted to reduce and eliminate regurgitation through valve 304, and thereby, valve 304 is repaired. For some applications, tether 34 is pulled or relaxed by manipulating stent 20, as is described hereinbelow.

For some applications, stent 20 is advanced toward and expanded in a portion of an inferior vena cava 308 (such as shown in FIGS. 5A-D) or a superior vena cava 310 (such as shown in FIGS. 1E-G of the above-mentioned '601 publication), i.e., a blood vessel that is in direct contact with a right atrium 306 of heart 302.

Figure 5A:
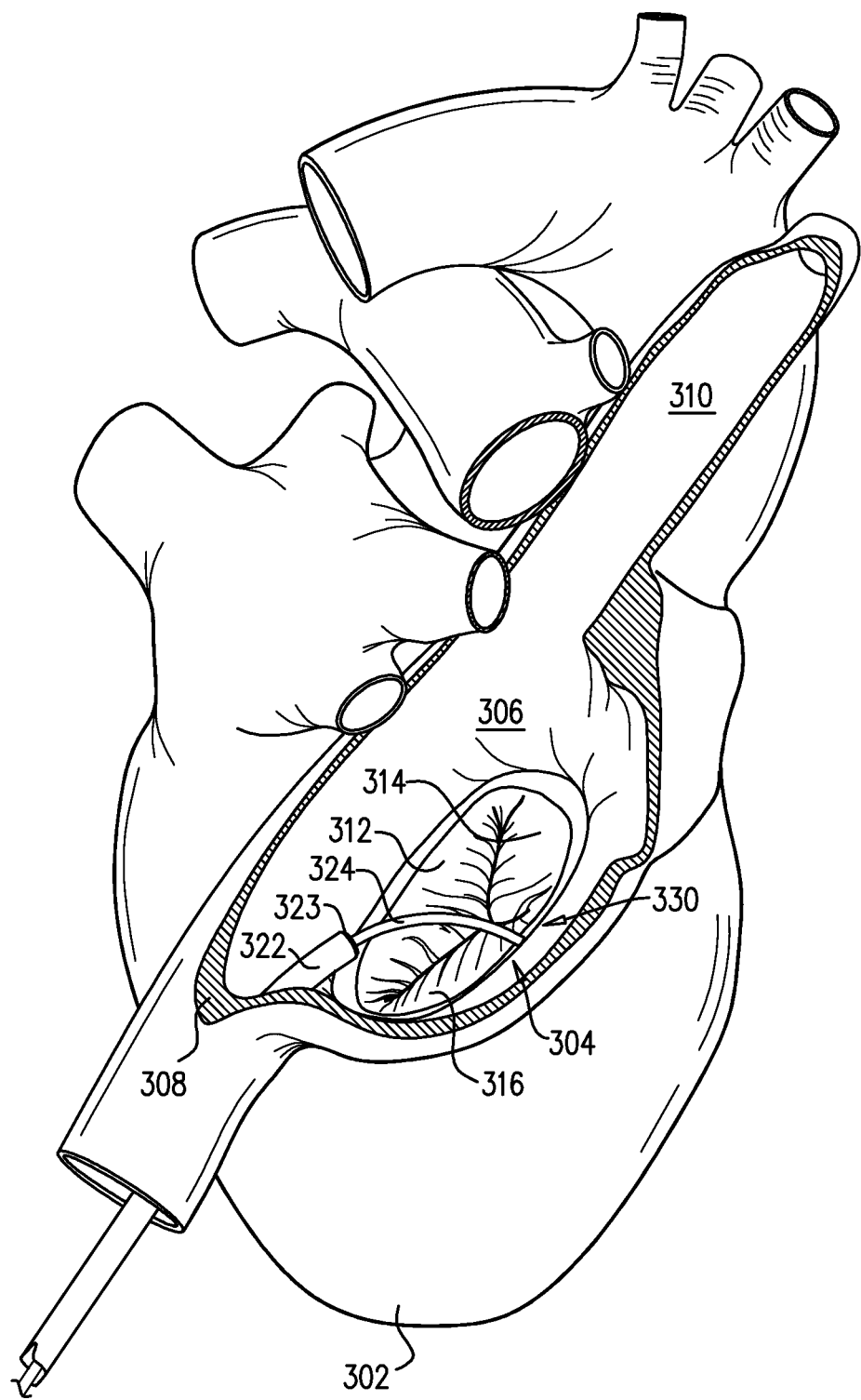
FIGS. 5A-D are schematic illustrations of an exemplary deployment of the anchoring system of FIG. 1 for repairing a tricuspid valve, in accordance with some applications of the present invention.

FIG. 5A shows the advancement of a catheter 322 toward atrium 306 until a distal end 323 of the catheter is disposed within atrium 306. The procedure is typically performed with the aid of imaging, such as fluoroscopy, transesophageal echo, and/or echocardiography. For some applications, the procedure begins by advancing a semi-rigid guidewire into right atrium 306 of the patient. The guidewire provides a guide for the subsequent advancement of catheter 322 therealong and into the right atrium. Catheter 322 typically comprises a 14-20 F sheath, although the size may be selected as appropriate for a given patient. Catheter 322 is advanced through vasculature into right atrium 306 using a suitable point of origin typically determined for a given patient, such as described in PCT Publication WO 2011/089601, which is assigned to the assignee of the present application and is incorporated herein by reference.

Once distal end 323 of catheter 322 is disposed within atrium 306, an anchor-deployment tube 324 is extended from within catheter 322 beyond distal end 323 thereof and toward a first implantation site 330. Anchor-deployment tube 324 holds tissue anchor 30 and a distal portion of tether 34. For some applications, tube 324 is steerable, as is known in the catheter art, while for other applications, a separate steerable element may be coupled to anchor-deployment tube 324. Under the aid of imaging guidance, anchor-deployment tube 324 is advanced toward first implantation site 330 until a distal end thereof contacts cardiac tissue of heart 302 at first implantation site 330. Anchor-deployment tube 324 facilitates atraumatic advancement of tissue anchor 30 toward first implantation site 330. For such applications in which anchor-deployment tube 324 is used, stent 20 is compressed within a portion of tube 324.

As shown, first implantation site 330 comprises a portion of an annulus of tricuspid valve 304. Implantation site 330 typically comprises a portion of the annulus of valve 304 that is between (1) the middle of the junction between the annulus and anterior leaflet 314, and (2) the middle of the junction between the annulus and posterior leaflet 316, e.g., between the middle of the junction between the annulus and anterior leaflet 314 and the commissure between the anterior and posterior leaflets. That is, tissue anchor 30 is coupled to, e.g., screwed into, the fibrous tissue of the tricuspid annulus close to the commissure in between anterior leaflet 314 and posterior leaflet 316. Implantation site 330 is typically close to the mural side of valve 304. For such applications, the drawing together of first and second implantation sites 330 and 352 cinches valve 304 and may create a bicuspidization of tricuspid valve 304, and thereby achieve stronger coaptation between anterior leaflet 314 and septal leaflet 312.

Figure 5B:
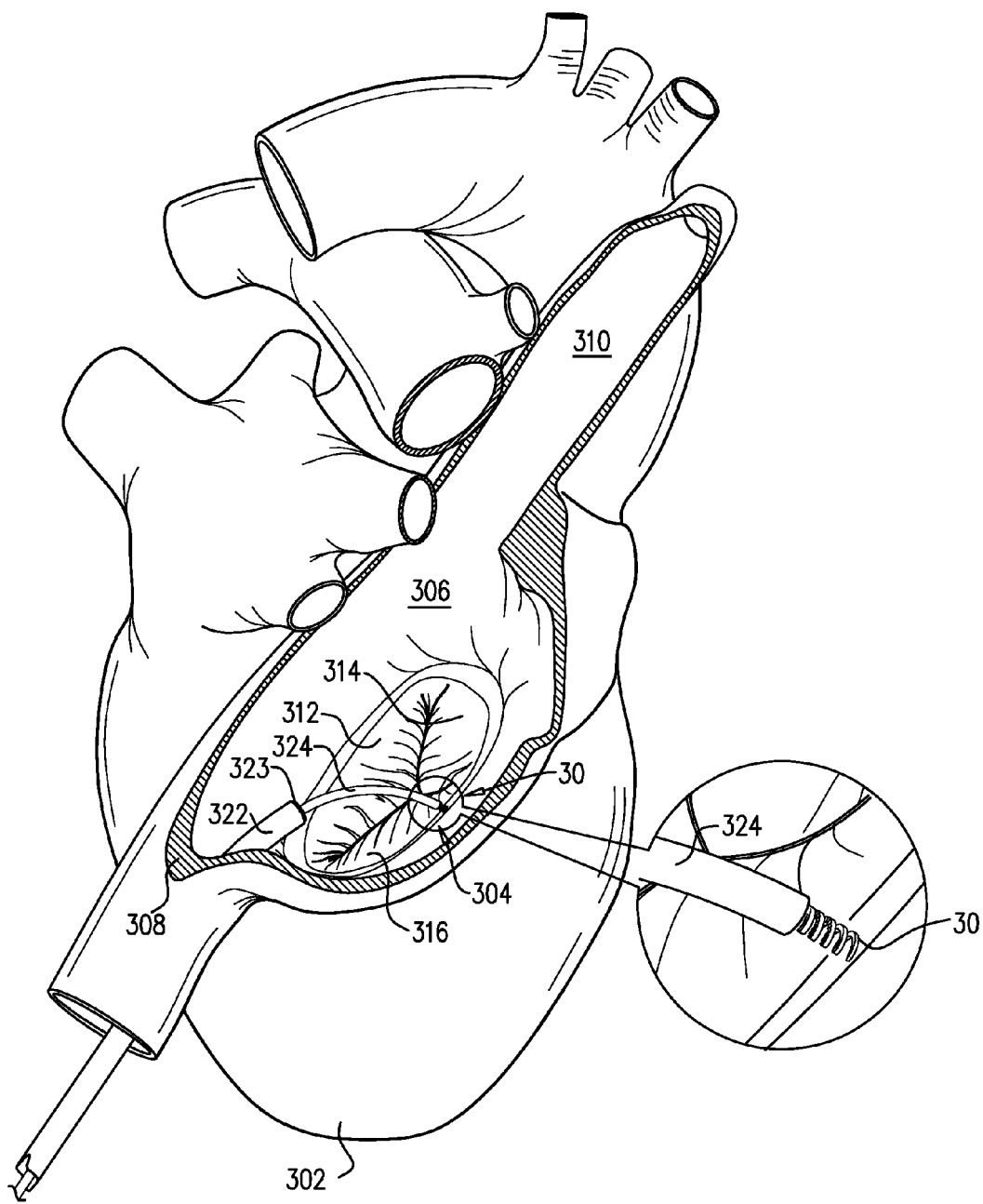

As shown in FIG. 5B, an anchor-manipulating tool (not shown for clarity of illustration), which is slidably disposed within anchor-deployment tube 324, is slid distally within tube 324 so as to push distally tissue anchor 30 and expose tissue anchor 30 from within tube 324. For some applications of the present invention, the anchor-manipulating tool is reversibly coupled to tissue anchor 30 and facilitates implantation of tissue anchor 30 in the cardiac tissue.

The physician rotates the anchor-manipulating tool from a site outside the body of the patient in order to rotate tissue anchor 30 and thereby screw at least a portion of tissue anchor 30 in the cardiac tissue. Alternatively, system 320 is provided independently of the anchor-manipulating tool, and anchor-deployment tube 324 facilitates implantation of tissue anchor 30 in the cardiac tissue. The physician rotates anchor-deployment tube 324 from a site outside the body of the patient in order to rotate tissue anchor 30 and thereby screw at least a portion of tissue anchor 30 in the cardiac tissue.

Figure 5C:
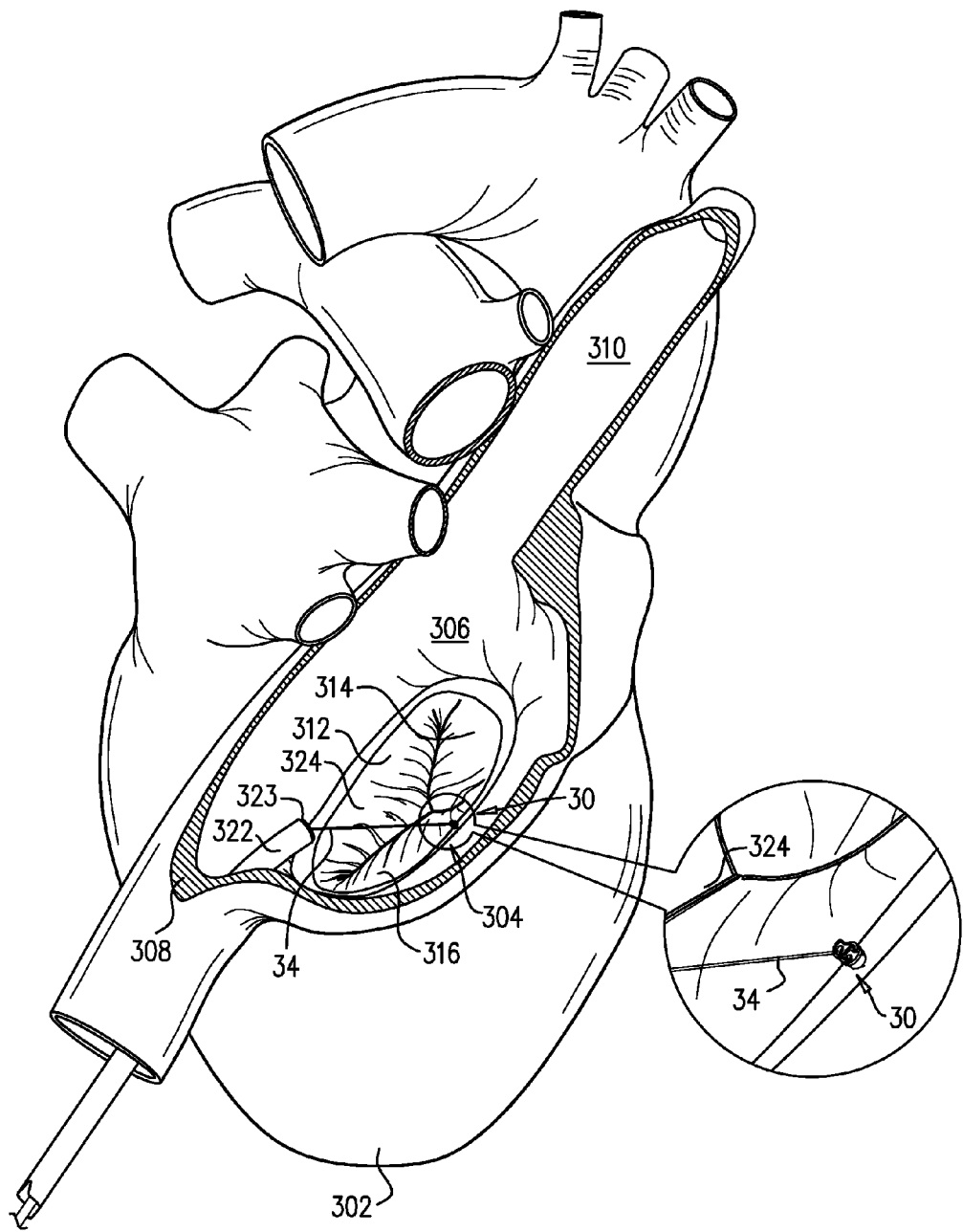

As shown in FIG. 5C, following the implantation of tissue anchor 30 at first implantation site 330, anchor-deployment tube 324 is retracted within catheter 322 in order to expose tether 34. Subsequently, tether 34 is tensioned in order to repair tricuspid valve 304, as described hereinbelow.

For some applications, prior to pulling the portion of tether 34 that is disposed between tissue anchor 30 and distal end 323 of catheter 322, a mechanism that facilitates the application of a pulling force to tether 34 is fixed in place, as described in the above-mentioned '601 publication.

For some applications, catheter 322 is reversibly coupled to a proximal portion of tether 34 by being directly coupled to the proximal portion of tether 34 and/or catheter 322 is reversibly coupled to stent 20. For example, catheter 322 may be reversibly coupled to stent 20 by the stent's application of a radial force against the inner wall of catheter 322 because of the tendency of stent 20 to expand radially. Following implantation of tissue anchor 30, catheter 322 (or an element disposed therein) is then pulled proximally to apply tension to tether 34, which, in such an application, functions as a tensioning element. For some applications, catheter 322 pulls on stent 20 in order to pull tether 34. For other applications, catheter 322 pulls directly on tether 34. For yet other applications, a pulling mechanism pulls on tether 34, as is described with reference to FIGS. 5A-D in the above-referenced '601 publication.

Pulling tether 34 pulls taut the portion of tether 34 that is disposed between tissue anchor 30 and distal end 323 of catheter 322. Responsively to the pulling of tether 34, at least the anterior and septal leaflets of tricuspid valve 304 are drawn together because the geometry of the annulus and/or of the wall of atrium 306 is altered in accordance with the pulling of tether 34 and depending on the positioning of tissue anchor 30.

For some applications, during the pulling of tether 34 by catheter 322, a level of regurgitation of tricuspid valve 304 is monitored. Tether 34 is pulled until the regurgitation is reduced or ceases. Once the physician determines that the regurgitation of valve 304 is reduced or ceases, and valve 304 has been repaired, the physician decouples catheter 322 from stent 20 disposed therein and/or from tether 34, and then retracts catheter 322 in order to expose stent 20. During the advancement of catheter 322 toward atrium 306, stent 20 is disposed within a distal portion of catheter 322 in a compressed state. Following initial retracting of catheter 322, stent 20 is exposed and is allowed to expand and contact a wall of inferior vena cava 308.

Figure 5D:
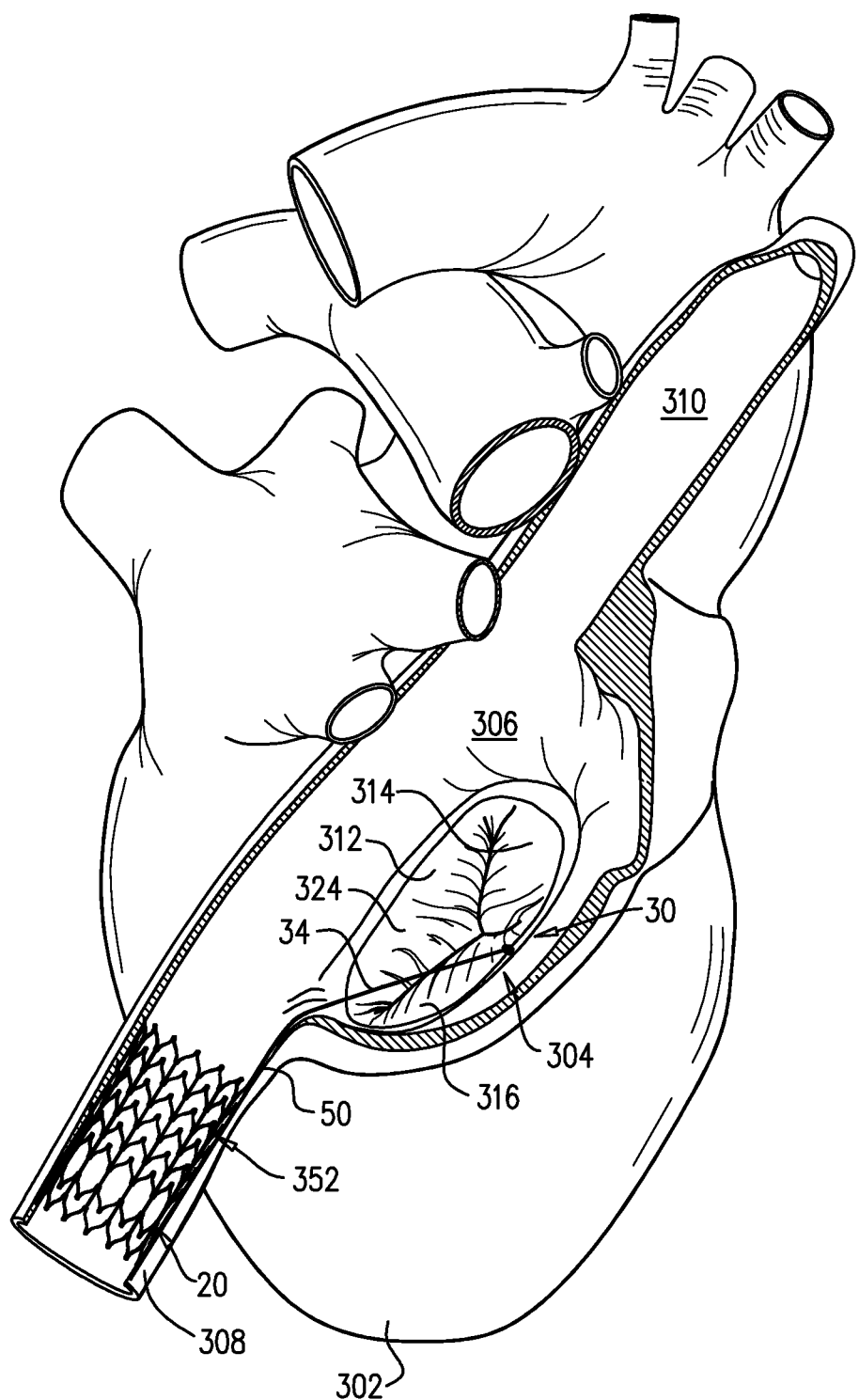

FIG. 5D shows stent 20 fully exposed and fully expanded, and thus implanted in inferior vena cava 308. Stent 20 maintains the tension of tether 34 on tissue anchor 30 and thereby on the portion of cardiac tissue to which tissue anchor 30 is coupled.

The techniques described with reference to FIGS. 5A-B may be performed in combination with techniques described in the above-mentioned '601 publication, mutatis mutandis.

As described above, for some applications the techniques described herein are used to repair the tricuspid valve. The techniques described herein may also be used to repair the mitral valve of the patient, mutatis mutandis.

Figure 6A:
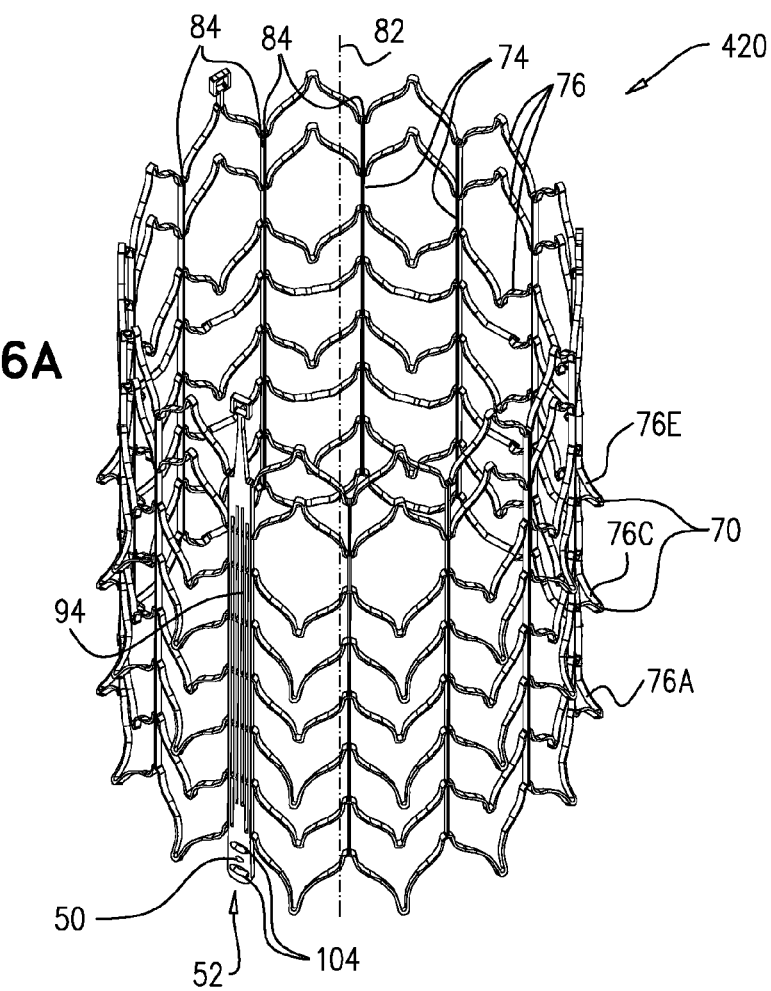
FIGS. 6A-B are schematic illustrations of yet another radially-expandable stent, in accordance with an application of the present invention.
Figure 6B:
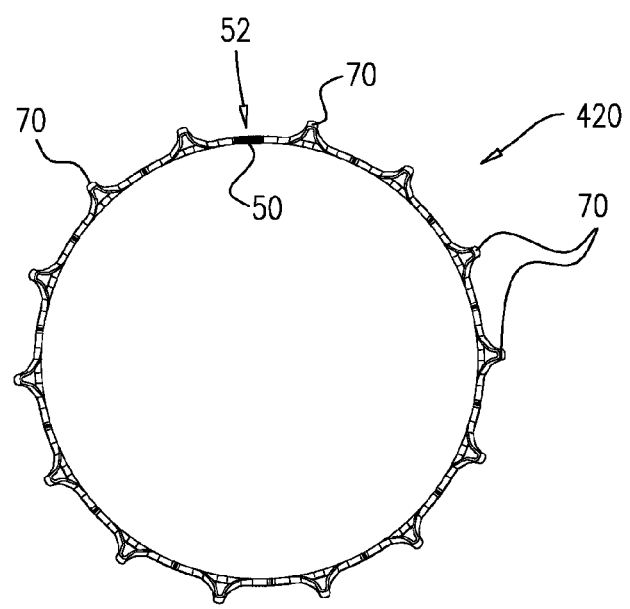

Reference is now made to FIGS. 6A-B, which are schematic illustrations of another radially-expandable stent 420, in accordance with an application of the present invention. FIGS. 6A and 6B are side- and end-views of stent 420, respectively. In this configuration, anchoring system 10 comprises radially-expandable stent 420, one or more tissue anchors 30, and one or more tethers 34 that connect the stent to the one or more tissue anchors. Other than as described below, stent 420 may have any of the features of stent 20, described hereinabove with reference to FIGS. 1 and 2A-D, stent 120, described hereinabove with reference to FIGS. 3A-D, and/or stent 220, described hereinabove with reference to FIGS. 4A-D.

Unlike stents 20, 120, and 220, stent 420 is not shaped so as to define lower-securement portion 56. Thus, the portion of stent 420 that includes one or more tether interfaces 50 (e.g., exactly one tether interface 50) at one or more tether circumferential locations 52 (e.g., at exactly one tether circumferential location 52) provides the same level of securement to the body lumen as do the other portions of the stent.

When stent 420 is unconstrained in the radially-expanded state (i.e., no forces are applied to the stent by a delivery tool, wall of a body vessel, or otherwise), only a portion of circumferential stent meanders 76 (e.g., exactly one, exactly two, exactly three (as shown), exactly four, or five or more of circumferential stent meanders 76) are shaped so as to define one or more outward protrusions. For example, first, third, and fifth distal circumferential stent meanders 76A, 76C, and 76E may define outward protrusions 70, and thus define respective polygons if projected onto the plane perpendicular to longitudinal axis 82 of stent 420. In contrast, the other circumferential stent meanders may not define any outward protrusions 70, and thus define respective circles if projected onto the plane perpendicular to longitudinal axis 82 of stent 420. Stent 420 may be shaped to define other polygon-circular shape patterns (e.g., every x circumferential stent meanders 76 may define outward protrusions, such as every second meander, or every third meander). Such providing of lower-securement axial spaces between circumferential stent meanders may facilitate better tissue fixation by scattering the protrusions.

For some applications, when stent 420 is unconstrained in the radially-expanded state, at least one of circumferential stent meanders 76 is shaped so as to define outward protrusions 70 circumferentially between one or more circumferentially-adjacent pairs 84 of columnar struts 74, such as between every circumferentially-adjacent pair of columnar struts 74. For some applications, exactly one, exactly two, exactly three (as shown and described above), exactly four, or five or more of circumferential stent meanders 76 are thus shaped.

For some applications, outward protrusions 70 are cascaded around stent 420.

Figure 7A:
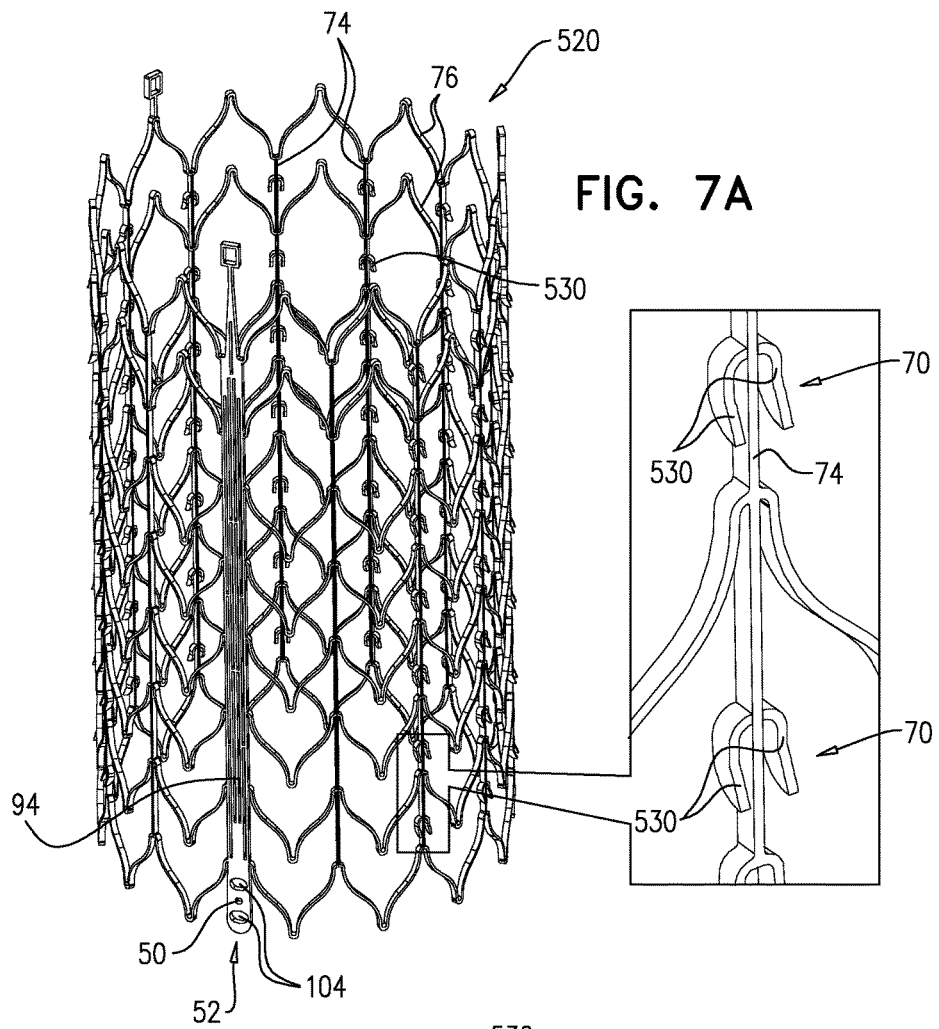
FIGS. 7A-B are schematic illustrations of a barbed configuration of the anchoring system of FIG. 1, in accordance with an application of the present invention.
Figure 7B:
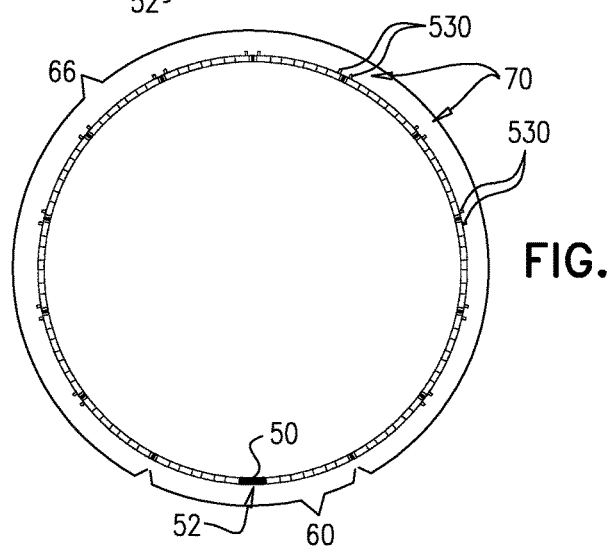

Reference is now made to FIGS. 7A-B, which are schematic illustrations of a barbed configuration of anchoring system 10, in accordance with an application of the present invention. In this configuration, anchoring system 10 comprises a radially-expandable stent 520, which is one configuration of stent 20 described hereinabove with reference to FIGS. 1 and 2A-D. As mentioned above, anchoring system 10 typically comprises one or more tissue anchors 30 and one or more tethers 34 that connect the stent to the one or more tissue anchors. Also as mentioned above, stent 20, when unconstrained in the radially-expanded state, is shaped so as to define one or more tether interfaces 50 at one or more tether circumferential locations 52, respectively.

In this configuration, unlike the configurations shown in the other figures, outward protrusions 70 are shaped so as to define respective barbs 530, when stent 520 is unconstrained in the radially-expanded state (i.e., no forces are applied to the stent by a delivery tool, wall of a body vessel, or otherwise). The barbs may aid in securing higher-securement portion 64 of stent 520 to the vessel wall. The barbs may protrude from one or more of columnar struts 74 of higher-securement portion 64, as shown, or from one or more of circumferential stent meanders 76 of higher-securement portion 64 (configuration not shown).

Medical Applications

The anchoring system and stents described herein may be used for a number of different medical applications, including but not limited to the following applications. For some of these applications, tissue anchors 30 and tethers 34 are not provided.

The anchor system and stents described herein may be used in tricuspid valve repair, such as described hereinabove with reference to FIGS. 5A-D. One of the stents may be used as an anchor point in the vena cava, to tether the tissue anchor which is coupled to the native valve (typically at the anterior-posterior commissure), thus lowering the anterior-posterior commissure and diminishing regurgitation.

The stents described herein may be used in aortic transcatheter valve implantation (TAVI), as a frame for the valve. The unique designs of the stent allow anchoring the prosthetic valve more securely to the native annulus, thereby preventing the prosthetic valve from migration at early and midterm follow-up. The stents described herein may also be used for mitral, pulmonary, and tricuspid replacement, using a transfemoral, transaxillary, transaortic, or transapical approach.

The stents described herein may be coupled to a filter, and may be used, for example, as a vena cava filter in patients suffering from a disorder of coagulation, in order to prevent pulmonary thromboembolism.

The stents described herein may be used as a transjugular intrahepatic portocaval shunt (TIPS) in patients suffering from cirrhosis and portal hypertension.

The stents described herein may be used for endoprosthesis placement in aortic abdominal and bisiliac vascular aneurism.

The stents described herein may be used for thoracic endovascular aortic repair (TEVAR) or for traditional open surgery elephant trunk or frozen elephant trunk technique in descending aortic thoracic and in Stanford Type A aortic dissection.

The stents described herein may be used for treating prostatic hypertrophy in patients suffering from prostate enlargement.

The stents described herein may be used be used to stent oncologic patients suffering from partial obstruction of the trachea.

As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally circular, or generally elliptical but not circular, or circular.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. application Ser. No. 12/692,061, filed Jan. 22, 2010, which published as US Patent Application Publication 2011/0184510;

International Application PCT/IL2011/000064, filed Jan. 20, 2011, which published as PCT Publication WO 2011/089601, and U.S. application Ser. No. 13/574,088 in the national stage thereof, which published as US Patent Application Publication 2013/0046380;

U.S. application Ser. No. 13/188,175, filed Jul. 21, 2011, which published as US Patent Application Publication 2012/0035712;

U.S. application Ser. No. 13/485,145, filed May 31, 2012, which published as US Patent Application Publication 2013/0325115;

U.S. application Ser. No. 13/553,081, filed Jul. 19, 2012, which published as US Patent Application Publication 2013/0018459;

International Application PCT/IL2012/000282, filed Jul. 19, 2012, which published as PCT Publication WO 2013/011502;

U.S. Provisional Application 61/750,427, filed Jan. 9, 2013, entitled, "Soft tissue anchors and implantation techniques"; and International Application PCT/IL2014/050027, filed Jan. 9, 2014, which published as PCT Publication WO 2014/108903.

In particular, the stents described herein may be used as one or more of the stents described in the above-listed applications, in combination with the other techniques described therein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with one or more tissue anchors and one or more tethers, the apparatus comprising:
   a radially-expandable stent, which, when unconstrained in a radially-expanded state, is generally tubular and shaped so as to define:
      one or more tether interfaces at one or more tether circumferential locations, respectively, each of which tether interfaces extends circumferentially contiguously around a portion of a circumference of the stent,
      a lower-securement portion that extends (a) along at least a contiguous lower-securement axial segment of the stent and (b) circumferentially around a contiguous lower-securement circumferential portion of the stent, which lower-securement axial segment and lower-securement circumferential portion include the one or more tether interfaces,
      a higher-securement portion that extends (a) along at least a contiguous higher-securement axial segment of the stent and (b) circumferentially around between 215 and 330 degrees of the circumference, at all circumferential locations other than those of the lower-securement circumferential portion, and
      a plurality of outward protrusions at respective circumferential locations around the higher-securement portion, and not around the lower-securement portion,
   wherein the lower-securement axial segment of the stent extends along at least 30% of an axial length of the stent, when the stent is unconstrained in the radially-expanded state.

2. The apparatus according to claim 1, wherein the one more tether interfaces comprise exactly one tether interface at exactly one tether circumferential location.

3. The apparatus according to claim 2, wherein the tether circumferential location is circumferentially centered in the lower-securement circumferential portion.

4. The apparatus according to claim 1, wherein the outward protrusions are rotationally-asymmetrically distributed around the circumference of the stent, when the stent is unconstrained in the radially-expanded state.

5. The apparatus according to claim 1, wherein the outward protrusions are periodically distributed around the higher-securement portion, when the stent is unconstrained in the radially-expanded state.

6. The apparatus according to claim 1, wherein the outward protrusions are blunt, when the stent is unconstrained in the radially-expanded state.

7. The apparatus according to claim 1, wherein the outward protrusions are shaped so as to define respective barbs, when the stent is unconstrained in the radially-expanded state.

8. The apparatus according to claim 1, wherein the higher-securement portion extends circumferentially around at least 270 degrees of the circumference of the stent, when the stent is unconstrained in the radially-expanded state.

9. The apparatus according to claim 8, wherein the higher-securement portion extends circumferentially around at least 300 degrees of the circumference of the stent, when the stent is unconstrained in the radially-expanded state.

10. The apparatus according to claim 1, wherein the higher-securement portion extends circumferentially around no more than 300 degrees of the circumference of the stent, when the stent is unconstrained in the radially-expanded state.

11. The apparatus according to claim 1, wherein each of the tether interfaces extends circumferentially contiguously around less than 30 degrees of the circumference of the stent.

12. The apparatus according to claim 1, wherein the apparatus further comprises the one or more tissue anchors.

13. The apparatus according to claim 1, wherein the apparatus further comprises the one or more tethers, which have respective first longitudinal portions that are coupled to the one or more tether interfaces, respectively.

14. The apparatus according to claim 13, wherein the apparatus further comprises the one or more tissue anchors, and wherein the one or more tethers have respective second longitudinal portions, different from the respective first longitudinal portions, which are coupled to the one or more tissue anchors, respectively.

15. The apparatus according to claim 13, wherein the stent is shaped so as to define one or more tension-distributing elements, which (a) extend along at least a tension-distribution axial segment of the stent at the one or more tether circumferential locations, respectively, (b) define the one or more tether interfaces, respectively, and (c) are configured to distribute tension applied by the one or more tethers, respectively, along the tension-distribution axial segment of the stent.

16. The apparatus according to claim 15, wherein the tension-distribution axial segment axially coincides with the lower-securement axial segment.

17. The apparatus according to claim 15, wherein the one or more tension-distributing elements and the stent are fabricated from a single unit.

18. The apparatus according to claim 15, wherein an axial length of each of the tension-distributing elements equals at least 15% of an axial length of the stent.

19. The apparatus according to claim 13, wherein the one or more tether interfaces are shaped so as to define one or more openings, respectively, through which the one or more tethers are respectively coupled.

20. Apparatus for use with one or more tissue anchors, the apparatus comprising:
a radially-expandable stent, which, when unconstrained in a radially-expanded state, is generally tubular and shaped so as to define:
one or more tether interfaces at one or more tether circumferential locations, respectively, each of which tether interfaces extends circumferentially contiguously around a portion of a circumference of the stent,
a lower-securement portion that extends (a) along at least a contiguous lower-securement axial segment of the stent and (b) circumferentially around a contiguous lower-securement circumferential portion of the stent, which lower-securement axial segment and lower-securement circumferential portion include the one or more tether interfaces,
a higher-securement portion that extends (a) along at least a contiguous higher-securement axial segment of the stent and (b) circumferentially around between 215 and 330 degrees of the circumference, at all circumferential locations other than those of the lower-securement circumferential portion, and
a plurality of outward protrusions at respective circumferential locations around the higher-securement portion, and not around the lower-securement portion,
wherein the apparatus further comprises one or more tethers, which have respective first longitudinal portions that are coupled to the one or more tether interfaces, respectively, and
wherein the stent is shaped so as to define one or more tension-distributing elements, which (a) extend along at least a tension-distribution axial segment of the stent at the one or more tether circumferential locations, respectively, (b) define the one or more tether interfaces, respectively, and (c) are configured to distribute tension applied by the one or more tethers, respectively, along the tension-distribution axial segment of the stent, and
wherein each of the one or more tension-distributing elements has a circumferential arc of between 1 and 15 degrees, when the stent is unconstrained in the radially-expanded state.

21. The apparatus according to claim 20, wherein the apparatus further comprises the one or more tissue anchors, and wherein the one or more tethers have respective second longitudinal portions, different from the respective first longitudinal portions, which are coupled to the one or more tissue anchors, respectively.

22. The apparatus according to claim 20, wherein the tension-distribution axial segment axially coincides with the lower-securement axial segment.

23. The apparatus according to claim 20, wherein the higher-securement portion extends circumferentially around at least 270 degrees of the circumference of the stent, when the stent is unconstrained in the radially-expanded state.

24. The apparatus according to claim 20, wherein each of the tether interfaces extends circumferentially contiguously around less than 30 degrees of the circumference of the stent.

25. Apparatus for use with one or more tissue anchors and one or more tethers, the apparatus comprising:
a radially-expandable stent, which, when unconstrained in a radially-expanded state, is generally tubular and shaped so as to define:
one or more tether interfaces at one or more tether circumferential locations, respectively, each of which tether interfaces extends circumferentially contiguously around a portion of a circumference of the stent,
a lower-securement portion that extends (a) along at least a contiguous lower-securement axial segment of the stent and (b) circumferentially around a contiguous lower-securement circumferential portion of the stent, which lower-securement axial segment and lower-securement circumferential portion include the one or more tether interfaces,
a higher-securement portion that extends (a) along at least a contiguous higher-securement axial segment of the stent and (b) circumferentially around between 215 and 330 degrees of the circumference, at all circumferential locations other than those of the lower-securement circumferential portion, and
a plurality of outward protrusions at respective circumferential locations around the higher-securement portion, and not around the lower-securement portion,
wherein an interior of the stent defines a right circular cylindrical shape having a radius, and wherein the outward protrusions extend radially outward from the cylindrical shape by a distance equal to between 5% and 25% of the radius, when the stent is unconstrained in the radially-expanded state.

26. The apparatus according to claim 25, wherein the lower-securement axial segment of the stent extends along at least 30% of an axial length of the stent, when the stent is unconstrained in the radially-expanded state.

27. The apparatus according to claim 25, wherein the apparatus further comprises the one or more tethers, which have respective first longitudinal portions that are coupled to the one or more tether interfaces, respectively.

28. The apparatus according to claim 27, wherein the apparatus further comprises the one or more tissue anchors, and wherein the one or more tethers have respective second longitudinal portions, different from the respective first longitudinal portions, which are coupled to the one or more tissue anchors, respectively.

29. The apparatus according to claim 27, wherein the stent is shaped so as to define one or more tension-distributing elements, which (a) extend along at least a tension-distribution axial segment of the stent at the one or more tether circumferential locations, respectively, (b) define the one or more tether interfaces, respectively, and (c) are configured to distribute tension applied by the one or more tethers, respectively, along the tension-distribution axial segment of the stent.

30. The apparatus according to claim 29, wherein the tension-distribution axial segment axially coincides with the lower-securement axial segment.

31. The apparatus according to claim 25, wherein the higher-securement portion extends circumferentially around at least 270 degrees of the circumference of the stent, when the stent is unconstrained in the radially-expanded state.

32. The apparatus according to claim 25, wherein each of the tether interfaces extends circumferentially contiguously around less than 30 degrees of the circumference of the stent.

33. Apparatus for use with one or more tissue anchors and one or more tethers, the apparatus comprising:

a radially-expandable stent, which, when unconstrained in a radially-expanded state, is generally tubular and shaped so as to define:
    one or more tether interfaces at one or more tether circumferential locations, respectively, each of which tether interfaces extends circumferentially contiguously around a portion of a circumference of the stent,
    a lower-securement portion that extends (a) along at least a contiguous lower-securement axial segment of the stent and (b) circumferentially around a contiguous lower-securement circumferential portion of the stent, which lower-securement axial segment and lower-securement circumferential portion include the one or more tether interfaces,
    a higher-securement portion that extends (a) along at least a contiguous higher-securement axial segment of the stent and (b) circumferentially around between 215 and 330 degrees of the circumference, at all circumferential locations other than those of the lower-securement circumferential portion, and
    a plurality of outward protrusions at respective circumferential locations around the higher-securement portion, and not around the lower-securement portion,
wherein the lower-securement portion has a circumferential arc that equals at least 200% of an average of circumferential distances between circumferential midpoints of circumferentially-adjacent ones of the outward protrusions around the higher-securement portion, when the stent is unconstrained in the radially-expanded state.

34. The apparatus according to claim 33, wherein the apparatus further comprises the one or more tethers, which have respective first longitudinal portions that are coupled to the one or more tether interfaces, respectively.

35. The apparatus according to claim 34, wherein the apparatus further comprises the one or more tissue anchors, and wherein the one or more tethers have respective second longitudinal portions, different from the respective first longitudinal portions, which are coupled to the one or more tissue anchors, respectively.

36. The apparatus according to claim 34, wherein the stent is shaped so as to define one or more tension-distributing elements, which (a) extend along at least a tension-distribution axial segment of the stent at the one or more tether circumferential locations, respectively, (b) define the one or more tether interfaces, respectively, and (c) are configured to distribute tension applied by the one or more tethers, respectively, along the tension-distribution axial segment of the stent.

37. The apparatus according to claim 36, wherein the tension-distribution axial segment axially coincides with the lower-securement axial segment.

38. The apparatus according to claim 33, wherein the higher-securement portion extends circumferentially around at least 270 degrees of the circumference of the stent, when the stent is unconstrained in the radially-expanded state.

39. The apparatus according to claim 33, wherein each of the tether interfaces extends circumferentially contiguously around less than 30 degrees of the circumference of the stent.

40. Apparatus for use with one or more tissue anchors and one or more tethers, the apparatus comprising:
    a radially-expandable stent, which, when unconstrained in a radially-expanded state, is generally tubular and shaped so as to define:
        one or more tether interfaces at one or more tether circumferential locations, respectively, each of which tether interfaces extends circumferentially contiguously around a portion of a circumference of the stent,
        a lower-securement portion that extends (a) along at least a contiguous lower-securement axial segment of the stent and (b) circumferentially around a contiguous lower-securement circumferential portion of the stent, which lower-securement axial segment and lower-securement circumferential portion include the one or more tether interfaces,
        a higher-securement portion that extends (a) along at least a contiguous higher-securement axial segment of the stent and (b) circumferentially around between 215 and 330 degrees of the circumference, at all circumferential locations other than those of the lower-securement circumferential portion, and
        a plurality of outward protrusions at respective circumferential locations around the higher-securement portion, and not around the lower-securement portion,
wherein the stent comprises a plurality of columnar struts and a plurality of circumferential stent meanders coupled to the columnar struts at respective axial locations, and
wherein one or more of the circumferential stent meanders are shaped so as to define the outward protrusions at the respective circumferential locations around the higher-securement portion, when the stent is unconstrained in the radially-expanded state.

41. The apparatus according to claim 40, wherein, when the stent is unconstrained in the radially-expanded state, at least one of the circumferential stent meanders is shaped so as to define (a) around the higher-securement portion, the outward protrusions, and (b) around the lower-securement portion, an arc of a circle if the circumferential stent meander is projected onto a plane perpendicular to a longitudinal axis of the stent.

42. The apparatus according to claim 40, wherein at least one of the circumferential stent meanders is shaped so as to define a plurality of apices, at least some of which are shaped so as to define the outward protrusions, when the stent is unconstrained in the radially-expanded state.

43. The apparatus according to claim 40, wherein the apparatus further comprises the one or more tethers, which have respective first longitudinal portions that are coupled to the one or more tether interfaces, respectively.

44. The apparatus according to claim 43, wherein the apparatus further comprises the one or more tissue anchors, and wherein the one or more tethers have respective second longitudinal portions, different from the respective first longitudinal portions, which are coupled to the one or more tissue anchors, respectively.

45. The apparatus according to claim 43, wherein the stent is shaped so as to define one or more tension-distributing elements, which (a) extend along at least a tension-distribution axial segment of the stent at the one or more tether circumferential locations, respectively, (b) define the one or more tether interfaces, respectively, and (c) are configured to distribute tension applied by the one or more tethers, respectively, along the tension-distribution axial segment of the stent.

46. The apparatus according to claim 45, wherein the tension-distribution axial segment axially coincides with the lower-securement axial segment.

47. The apparatus according to claim 40, wherein the higher-securement portion extends circumferentially around at least 270 degrees of the circumference of the stent, when the stent is unconstrained in the radially-expanded state.

48. The apparatus according to claim 40, wherein each of the tether interfaces extends circumferentially contiguously around less than 30 degrees of the circumference of the stent.

* * * * *